(12) United States Patent
Foley et al.

(10) Patent No.: US 10,111,755 B2
(45) Date of Patent: Oct. 30, 2018

(54) EXPANDING INTERBODY IMPLANT AND ARTICULATING INSERTER AND METHODS OF USE

(71) Applicant: Warsaw Orthopedic, Inc, Warsaw, IN (US)

(72) Inventors: Kevin T. Foley, Germantown, TN (US); Roy K. Lim, Germantown, TN (US); Matthew M. Morrison, Cordova, TN (US); Jonathan M. Dewey, Memphis, TN (US)

(73) Assignee: Warsaw, Orthopedic, Inc., Warsaw, IN (US)

( * ) Notice: Subject to any disclaimer, the term of this patent is extended or adjusted under 35 U.S.C. 154(b) by 0 days.

(21) Appl. No.: 15/442,101

(22) Filed: Feb. 24, 2017

(65) Prior Publication Data

US 2018/0243107 A1 Aug. 30, 2018

(51) Int. Cl.
*A61F 2/44* (2006.01)
*A61F 2/30* (2006.01)

(52) U.S. Cl.
CPC .......... *A61F 2/4425* (2013.01); *A61F 2/4465* (2013.01); *A61F 2002/30398* (2013.01); *A61F 2002/30579* (2013.01); *A61F 2002/443* (2013.01); *A61F 2002/4475* (2013.01)

(58) Field of Classification Search
CPC .................. A61F 2/4425; A61F 2/4465; A61F 2002/30398; A61F 2002/30579; A61F 2002/443; A61F 2002/4475
USPC ............ 623/17.15, 17.16; 606/246, 99, 86 A
See application file for complete search history.

(56) References Cited

U.S. PATENT DOCUMENTS

| | | | |
|---|---|---|---|
| 4,743,256 A | 5/1988 | Brantigan |
| 4,834,757 A | 5/1989 | Brantigan |
| 4,863,476 A | 9/1989 | Shepperd |
| 4,878,915 A | 11/1989 | Brantigan |
| 5,171,278 A | 12/1992 | Pisharodi |
| 5,192,327 A | 3/1993 | Brantigan |
| 5,425,772 A | 6/1995 | Brantigan |
| 5,443,514 A | 8/1995 | Steffee |
| 5,484,437 A | 1/1996 | Michelson |

(Continued)

FOREIGN PATENT DOCUMENTS

| | | | |
|---|---|---|---|
| FR | 2817463 A1 | 6/2002 |
| FR | 2824261 A1 | 11/2002 |

(Continued)

*Primary Examiner* — Pedro Philogene
*Assistant Examiner* — David C Comstock

(57) ABSTRACT

A device includes an upper endplate having an engagement surface, an inner surface and first projections extending from the inner surface. The first projections each include a first inclined surface. A lower endplate includes an engagement surface, an inner surface and second projections extending from the inner surface. The second projections each include a second inclined surface. A wedge is positioned between the endplates. The wedge includes first mating parts that engage the first inclined surfaces and second mating parts that engage the second inclined surfaces. The wedge is movable relative to the endplates to move the device between a first configuration having a first height between the engagement surfaces and a second configuration having an increased second height between the engagement surfaces. Methods of use are disclosed.

17 Claims, 18 Drawing Sheets

(56) References Cited

U.S. PATENT DOCUMENTS

| | | |
|---|---|---|
| 5,505,732 A | 4/1996 | Michelson |
| 5,522,899 A | 6/1996 | Michelson |
| 5,554,191 A | 9/1996 | Lahille |
| D377,096 S | 12/1996 | Michelson |
| 5,609,635 A | 3/1997 | Michelson |
| 5,653,763 A | 8/1997 | Errico et al. |
| 5,658,335 A | 8/1997 | Allen |
| 5,665,122 A | 9/1997 | Kambin |
| 5,716,415 A | 2/1998 | Steffee |
| 5,755,732 A | 5/1998 | Green et al. |
| 5,766,252 A | 6/1998 | Henry et al. |
| 5,776,199 A | 7/1998 | Michelson |
| 5,782,830 A | 7/1998 | Farris |
| 5,865,848 A | 2/1999 | Baker |
| 5,888,224 A | 3/1999 | Beckers et al. |
| 5,888,227 A | 3/1999 | Cottle |
| 5,893,889 A | 4/1999 | Harrington |
| 5,895,426 A | 4/1999 | Scarborough et al. |
| 5,980,522 A | 11/1999 | Koros et al. |
| 5,984,922 A | 11/1999 | McKay |
| 6,045,579 A | 4/2000 | Hochshuler et al. |
| 6,080,158 A | 6/2000 | Lin |
| 6,080,193 A | 6/2000 | Hochshuler et al. |
| 6,090,143 A | 7/2000 | Meriwether et al. |
| 6,102,950 A | 8/2000 | Vaccaro |
| 6,113,638 A | 9/2000 | Williams et al. |
| 6,117,174 A | 9/2000 | Nolan |
| 6,159,245 A | 12/2000 | Meriwether et al. |
| 6,176,881 B1 | 1/2001 | Schaer et al. |
| 6,176,882 B1 | 1/2001 | Biedermann et al. |
| 6,183,517 B1 | 2/2001 | Suddaby |
| 6,190,414 B1 | 2/2001 | Young et al. |
| 6,217,579 B1 | 4/2001 | Koros |
| 6,245,108 B1 | 6/2001 | Biscup |
| 6,319,257 B1 | 11/2001 | Carignan et al. |
| 6,368,351 B1 | 4/2002 | Glenn et al. |
| 6,371,989 B1 | 4/2002 | Chauvin et al. |
| 6,419,705 B1 | 7/2002 | Erickson |
| 6,419,706 B1 | 7/2002 | Graf |
| 6,432,108 B1 | 8/2002 | Burgess et al. |
| 6,436,140 B1 | 8/2002 | Liu et al. |
| 6,436,142 B1 | 8/2002 | Paes et al. |
| 6,443,989 B1 | 9/2002 | Jackson |
| 6,454,806 B1 | 9/2002 | Cohen et al. |
| 6,454,807 B1 | 9/2002 | Jackson |
| 6,468,276 B1 | 10/2002 | McKay |
| 6,517,051 B1 | 2/2003 | Cavanaugh |
| 6,562,074 B2 | 5/2003 | Gerbec et al. |
| 6,576,016 B1 | 6/2003 | Hochshuler et al. |
| 6,641,614 B1 | 11/2003 | Wagner et al. |
| 6,676,703 B2 | 1/2004 | Biscup |
| 6,706,070 B1 | 3/2004 | Wagner et al. |
| 6,767,366 B2 | 7/2004 | Lee et al. |
| 6,830,589 B2 | 12/2004 | Erickson |
| 6,852,129 B2 | 2/2005 | Gerbec et al. |
| 6,893,464 B2 | 5/2005 | Kiester |
| 7,828,849 B2 | 11/2010 | Lim |
| 8,579,981 B2 | 11/2013 | Lim et al. |
| 8,986,389 B2 | 3/2015 | Lim et al. |
| 9,271,846 B2 | 3/2016 | Lim et al. |
| 9,445,919 B2 | 9/2016 | Palmatier et al. |
| 2001/0032020 A1 | 10/2001 | Besselink |
| 2002/0010511 A1 | 1/2002 | Michelson |
| 2002/0045943 A1 | 4/2002 | Uk |
| 2002/0045945 A1 | 4/2002 | Liu et al. |
| 2002/0068976 A1 | 6/2002 | Jackson |
| 2002/0068977 A1 | 6/2002 | Jackson |
| 2002/0128713 A1 | 9/2002 | Ferree |
| 2002/0128716 A1 | 9/2002 | Cohen et al. |
| 2002/0138146 A1 | 9/2002 | Jackson |
| 2002/0143401 A1 | 10/2002 | Michelson |
| 2002/0177897 A1 | 11/2002 | Michelson |
| 2003/0139812 A1 | 7/2003 | Garcia et al. |
| 2003/0149484 A1 | 8/2003 | Michelson |
| 2004/0059421 A1 | 3/2004 | Glenn et al. |
| 2004/0087947 A1 | 5/2004 | Lim et al. |
| 2004/0102847 A1 | 5/2004 | Sato et al. |
| 2004/0127993 A1 | 7/2004 | Kast et al. |
| 2004/0127994 A1 | 7/2004 | Kast et al. |
| 2010/0292796 A1* | 11/2010 | Greenhalgh ........ A61B 17/8858 623/17.11 |
| 2013/0023994 A1* | 1/2013 | Glerum .................... A61F 2/447 623/17.16 |
| 2016/0256291 A1* | 9/2016 | Miller ...................... A61F 2/447 |
| 2017/0014240 A1* | 1/2017 | Seifert .................... A61F 2/447 |
| 2017/0165083 A1* | 6/2017 | Greenhalgh ............ A61F 2/447 |
| 2017/0296353 A1* | 10/2017 | Matthis .................. A61F 2/4425 |
| 2018/0042732 A1* | 2/2018 | Seifert .................. A61F 2/4425 |

FOREIGN PATENT DOCUMENTS

| | | |
|---|---|---|
| WO | 9700054 A1 | 1/1997 |
| WO | 9848738 A1 | 11/1998 |
| WO | 9932054 A1 | 7/1999 |
| WO | 9942062 A1 | 8/1999 |
| WO | 0074605 A1 | 12/2000 |
| WO | 0238062 A2 | 5/2002 |
| WO | 03092507 A2 | 11/2003 |
| WO | 2004019829 A1 | 3/2004 |

* cited by examiner

EXPANDING INTERBODY IMPLANT AND ARTICULATING INSERTER AND METHODS OF USE

TECHNICAL FIELD

The present disclosure generally relates to medical devices, systems and methods for the treatment of musculoskeletal disorders, and more particularly to an expandable interbody implant system and method for treating a vertebral column.

BACKGROUND

Spinal disorders such as degenerative disc disease, disc herniation, osteoporosis, spondylolisthesis, stenosis, scoliosis and other curvature abnormalities, kyphosis, tumor, and fracture may result from factors including trauma, disease and degenerative conditions caused by injury and aging. Spinal disorders typically result in symptoms including pain, nerve damage, and partial or complete loss of mobility. For example, after a disc collapse, severe pain and discomfort can occur due to the pressure exerted on nerves and the spinal column.

Non-surgical treatments, such as medication, rehabilitation and exercise can be effective, however, may fail to relieve the symptoms associated with these disorders. Surgical treatment of these spinal disorders includes fusion, fixation, discectomy, laminectomy and implantable prosthetics. These treatments may employ interbody implants. This disclosure describes an improvement over these prior art technologies.

SUMMARY

Accordingly, an expandable interbody implant system and method are disclosed. In one embodiment, the system includes a device to space apart vertebral members. The device comprises an upper endplate comprising a first engagement surface configured to engage a first vertebra and an opposite inner surface. The upper endplate comprises first projections extending from the inner surface. The first projections each comprise a first inclined surface. A lower endplate comprises a second engagement surface configured to engage a second vertebra that is adjacent to the first vertebra and an opposite inner surface. The lower endplate comprises second projections extending from the inner surface of the lower endplate. The second projections each comprise a second inclined surface. A wedge is positioned between the endplates. The wedge comprises first mating parts that engage the first inclined surfaces and second mating parts that engage the second inclined surfaces. The wedge is movable relative to the endplates to move the device between a first configuration having a first height between the engagement surfaces and a second configuration having an increased second height between the engagement surfaces.

BRIEF DESCRIPTION OF THE DRAWINGS

The present disclosure will become more readily apparent from the specific description accompanied by the following drawings, in which.

DETAILED DESCRIPTION

Figure 1:
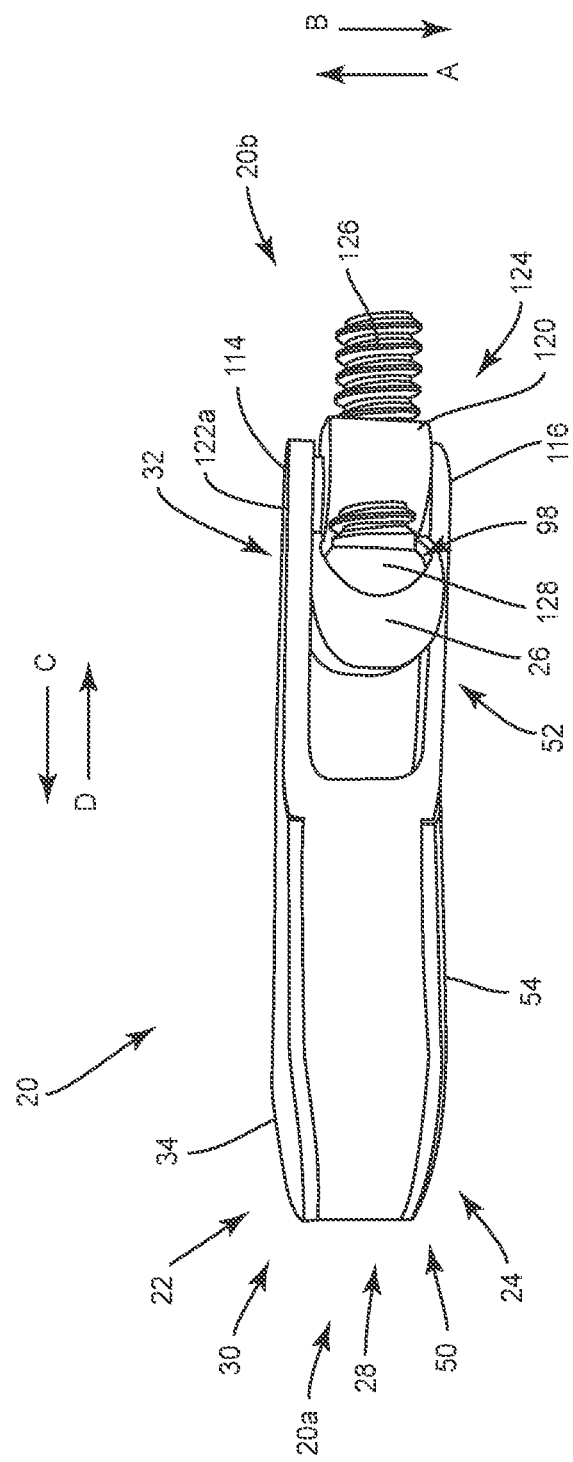
FIG. 1 is a side view of one embodiment of an implant of a system in accordance with the principles of the present disclosure.

The exemplary embodiments of an expandable interbody implant system and related methods of use disclosed herein are discussed in terms of medical devices for the treatment of musculoskeletal disorders and more particularly, in terms of an expandable interbody implant system and related methods for treating a vertebral column. It is envisioned that the implant system may provide, for example, fusion, decompression, restoration of sagittal balance and resistance of subsidence into tissue, such as, for example, surfaces of vertebral endplates. It is further envisioned that the system includes an interbody implant that expands after insertion into an intervertebral disc space and has several features, such as, for example, facile insertion into the intervertebral disc space such that less bone removal is necessary during a surgical procedure, decompression of nerve roots, and expansion to restore sagittal balance such that more expansion is provided on an anterior side relative to a posterior side in for example, a lumbar application. In some embodiments, the interbody implant can be inserted into the intervertebral disc space using a passive (e.g., non-steerable) or active (e.g., steerable) inserter. In some embodiments, the interbody implant is configured to be inserted at about a 15 degree angle and can be articulated to an angle of about 75 degrees to 100 degrees. This arrangement allows for continuous angulation, which allows implant deployment at any angle from about 15 through 85-90 degrees. In some embodiments, articulation is achieved through the use of a pivot that is secured to a frame of the implant. In some embodiments, the pivot is secured to the frame using pivot plugs. In some embodiments, the interbody implant can be deployed at any insertion angle. In some embodiments, the interbody implant can be deployed at any angle from about 15 to about 85-90 degrees. In some embodiments, the expandable interbody implant has a 32 millimeter (mm) by 13.5 mm footprint. In some embodiments, the expandable interbody implant has a maximum insertion footprint of about 13.5 mm at 15 degrees.

In some embodiments, the expandable interbody implant has an undeployed height and can be expanded to a deployed height. In some embodiments, the deployed height is less than twice the undeployed height. In some embodiments, the deployed height is twice the undeployed height. In some embodiments, the deployed height is greater than twice the undeployed height. In some embodiments, the expandable interbody implant has an undeployed height of about 7 mm and can be expanded to a deployed height of about 14 mm. In some embodiments, the expandable interbody implant has an undeployed height of about 8 mm and can be expanded to a deployed height of about 16 mm. In some embodiments, the expandable interbody implant has an undeployed height of about 9 mm and can be expanded to a deployed height of about 18 mm. In some embodiments, the expandable interbody implant has an undeployed height of about 10 mm and can be expanded to a deployed height of about 20 mm. In some embodiments, the expandable interbody implant is deployed using a drive screw to move the implant from the undeployed height to the deployed height. The drive screw threads into the pivot discussed herein. In some embodiments, the drive screw comprises a ball tip that is positioned in a circular or semi-circular trough in a wedge of the implant, wherein unscrewing the ball tipped screw retracts the wedge and undeploys the implant. In some embodiments, the expandable interbody implant may be incrementally deployed from the undeployed height to the deployed height.

In some embodiments, the expandable interbody implant includes implant endplates, such as, for example, upper and lower implant endplates each having ramps that engage ramps of the wedge. That is, each of the implant endplates includes multiple ramps. The wedge includes an upper surface with multiple ramps that engage the ramps of the upper endplate and a lower surface with multiple ramps that engage the ramps of the lower endplate. The wedge moves relative to the endplates to move the ramps of the endplates along the ramps of the wedge to move the implant from the undeployed height to the deployed height. As the wedge moves away from the pivot, endplate deployment is achieved. The ramps are staggered such that opposing ramps are not aligned or mirrored. The relative position of the implant endplates with respect to the pivot is maintained by the frame. In some embodiments, at least one of the ramps of the wedge extends into and is flush with a vertebral engaging surface of one of the implant endplates when the implant is undeployed. In some embodiments, the ramps of the wedge poke into the implant endplate when the implant is undeployed. In some embodiments, the ramps of the implant endplate reside on the ramps of the wedge when the implant is fully deployed. In some embodiments, the ramps of the implant endplate reside on the ramps of the wedge when the implant is fully deployed. In some embodiments, the ramps have symmetrical geometry to allow the endplates to be driven into a parallel relationship. In some embodiments, the ramps have asymmetrical geometry to allow the endplates to be driven into a non-parallel relationship (kyphosis or lordosis). In some embodiments, the ramps have asymmetrical geometry to allow the endplates to simultaneously correct sagittal and coronal imbalance while restoring interbody height.

In some embodiments, at least 0.5 mm bearing contact of the ramps of the implant endplate and the ramps of the wedge is maintained when the implant is fully deployed. In some embodiments, the implant endplate comprises endplate tabs that include outriggers, such as, for example, supplemental side ramps that engage grooves of the wedge as the implant moves from the undeployed height to the deployed height. In some embodiments, the supplemental side ramps engage the grooves of the wedge when the implant is fully deployed. In some embodiments, the supplemental side ramps allow the implant to close during undeployment. In some embodiments, the ramps of the implant are long ramps that extend into implant endplates of the implant and below a centerline of the implant to ensure 0.5 mm of implant ramp bearing contact at full deployment while allowing the deployment height to be at least twice the undeployed height. The lengths of the ramps extending past the centerline of the implant are load bearing areas, which provide implant strength. In some embodiments, the implant endplates include tabs that are indexed into rails in the frame for relative positioning. The tabs of each implant endplate are spaced apart by a gap. The tabs move up and down within the rails as the implant moves between the undeployed height and the deployed height.

In some embodiments, the expandable interbody implant is kidney shaped and defines a curve of radii X. The wedge travels along radii X as the implant moves between the undeployed and deployed heights. In some embodiments, all ramps, outriggers and features converge to the center of radii X in order to function, while avoiding binding. In some embodiments, the radii can be infinity and the implant is a straight implant. In some embodiments, the expandable interbody implant is rectangular, bullet-shaped, kidney-shaped, lordotic or kyphotic-shaped.

In some embodiments, the expandable interbody implant system is employed with a posterior approach to the intervertebral disc space. In some embodiments, the expandable interbody implant has a titanium construction. In some embodiments, the expandable interbody implant is closable. In some embodiments, the expandable interbody implant has a thru design that defines a graft pocket configured for disposal of a bone graft, for example. In some embodiments, the expandable interbody implant has multiple windows for entry of graft material into a cage defined by the implant. In some embodiments, the expandable interbody implant has textured upper and lower surfaces for improved gripping of vertebral surfaces.

It is envisioned that the expandable interbody implant and methods of use disclosed herein can be employed to obtain fusion of vertebrae through a minimally invasive or percutaneous technique. In one embodiment, the disclosed expandable interbody implant and methods of use can provide improved spinal treatment with a device that is made to expand vertically to create lordosis in vertebrae. It is contemplated that the expandable interbody implant and methods of use disclosed herein provide a cavity of relatively large volume for post-packing of at least one agent, for example, bone graft.

It is envisioned that the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. It is contemplated that the present disclosure may be employed with other osteal and bone related applications, including those associated with diagnostics and therapeutics. It is further contemplated that the disclosed expandable interbody implant may be alternatively employed in a surgical treatment with a patient in a prone or supine position, and/or employ various surgical approaches to the spine, including anterior, posterior, posterior mid-line, medial, lateral, postero-lateral, and/or antero-lateral approaches, and in other body regions. The expandable interbody implant of the present disclosure may also be alternatively employed with procedures for treating the lumbar, cervical, thoracic and pelvic regions of a spinal column. The expandable interbody implant and methods of the present disclosure may also be used on animals, bone models and other non-living substrates, such as, for example, in training, testing and demonstration.

The present disclosure may be understood more readily by reference to the following detailed description of the disclosure taken in connection with the accompanying drawing figures, which form a part of this disclosure. It is to be understood that this disclosure is not limited to the specific devices, methods, conditions or parameters described and/or shown herein, and that the terminology used herein is for the purpose of describing particular embodiments by way of example only and is not intended to be limiting of the claimed disclosure. Also, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, outer, inner, terminal (denoting position or location), left and right, posterior, anterior, and the like, are for illustrative purposes only and can be varied within the scope of the disclosure. For example, the references "superior" and "inferior" are relative and used only in the context to the other, and are not necessarily "upper" and "lower".

Further, as used in the specification and including the appended claims, "treating" or "treatment" of a disease or condition refers to performing a procedure that may include administering one or more drugs to a patient in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (for example, preventing the disease from occurring in a patient, who may be predisposed to the disease but has not yet been diagnosed as having it).

In addition, treating or treatment does not require complete alleviation of signs or symptoms, does not require a cure, and specifically includes procedures that have only a marginal effect on the patient. Treatment can include inhibiting the disease, for example, arresting its development, or relieving the disease, for example, causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

The following discussion includes a description of an expandable interbody implant and related methods of employing the expandable interbody implant in accordance with the principles of the present disclosure. Alternate embodiments are also disclosed. Reference will now be made in detail to the exemplary embodiments of the present disclosure, which are illustrated in the accompanying figures. Turning now to FIGS. 1-18, there are illustrated components of an interbody implant system including an intervertebral implant 20 in accordance with the principles of the present disclosure.

The components of the system can be fabricated from biologically acceptable materials suitable for medical applications, including metals, synthetic polymers, ceramics and bone material and/or their composites, depending on the particular application and/or preference of a medical practitioner. For example, the components of the system, individually or collectively, can be fabricated from materials such as stainless steel alloys, commercially pure titanium, titanium alloys, Grade 5 titanium, super-elastic titanium alloys, cobalt-chrome alloys, stainless steel alloys, super-elastic metallic alloys (for example, Nitinol, super elasto-plastic metals, such as GUM METAL® manufactured by Toyota Material Incorporated of Japan), ceramics and composites thereof such as calcium phosphate (for example, SKELITE™ manufactured by Biologix Inc.), thermoplastics such as polyaryl ether ketone (PAEK) including polyether ether ketone (PEEK), polyether ketone ketone (PEKK) and polyetherketone (PEK), carbon-PEEK composites, PEEK-$BaSO_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyimide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polylactide, polyglycolide, polytyrosine carbonate, polycaprolactone and their combinations. Various components of the system may be fabricated from material composites, including the above materials, to achieve various desired characteristics such as strength, rigidity, elasticity, flexibility, compliance, biomechanical performance, durability and radiolucency or imaging preference. The components of the system, individually or collectively, may also be fabricated from a heterogeneous material such as a combination of two or more of the above-described materials.

The system including intervertebral implant 20 can be employed as a stabilization device in fusion and fixation procedures, for example, for patients suffering from a spinal disorder to provide height restoration between vertebral bodies, decompression, restoration of sagittal balance and/or resistance of subsidence into vertebral endplates. The components of the interbody implant system may be monolithically formed, integrally connected or include fastening elements and/or instruments, for example, as described herein.

Figure 2:
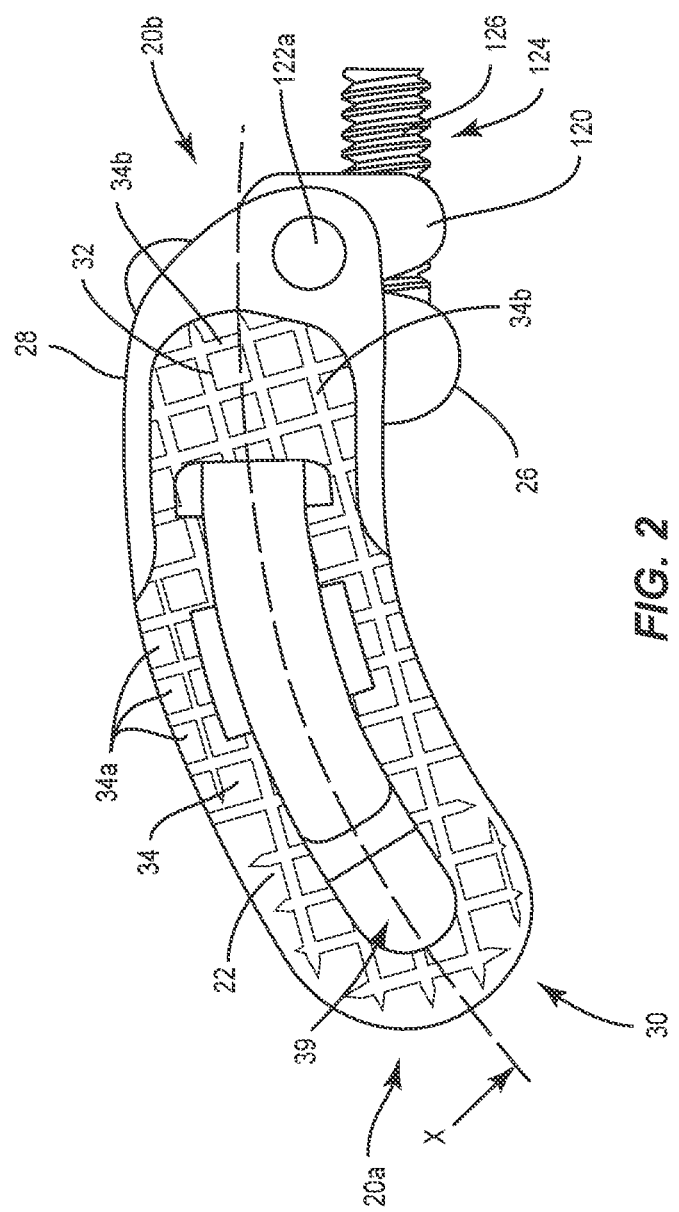
FIG. 2 is a top view of the implant shown in FIG. 1.

Intervertebral implant 20 comprises an implant endplate 22, an opposite implant endplate 24 and a wedge 26 positioned between endplates 22, 24. Endplates 22, 24 and wedge 26 are positioned within a frame 28 of implant 20, as discussed herein. Wedge 26 is configured to translate relative to endplates 22, 24 to move implant 20 between an undeployed or unexpanded configuration, shown in FIGS. 1 and 2, and a deployed or expanded configuration, shown in FIGS. 3 and 4. In some embodiments, implant 20 is kidney-shaped and extends between a first end 20a and an opposite second end 20b along a radius, such as, for example an arc X, as shown in FIGS. 1 and 2. In some embodiments, arc X has a continuous radius of curvature. In some embodiments, arc X has a variable radius of curvature. In some embodiments, implant 20 is square, rectangular, oval, bullet-shaped, lordotic or kyphotic-shaped. In some embodiments, implant 20 is made from one or more of the materials discussed herein. In some embodiments, implant 20 is made from a metal, such as, for example, titanium. In some embodiments, implant 20 consists of one or more materials incorporated on one or more parts of the implant, for example titanium ramps with a PEEK endplate.

Figure 5:
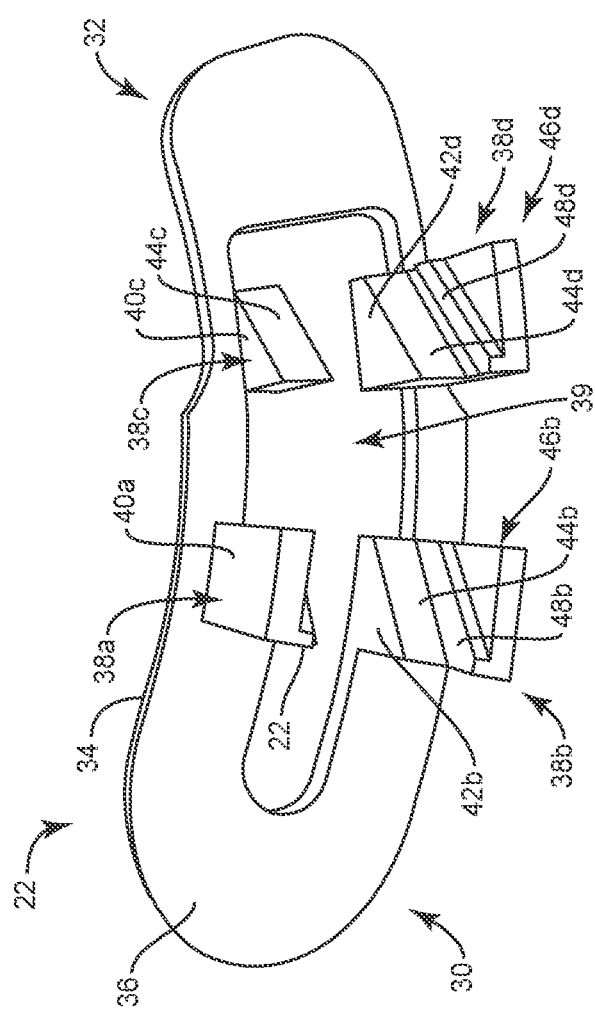
FIG. 5 is a bottom, perspective view of a component of the implant shown in FIG. 1.
Figure 6:
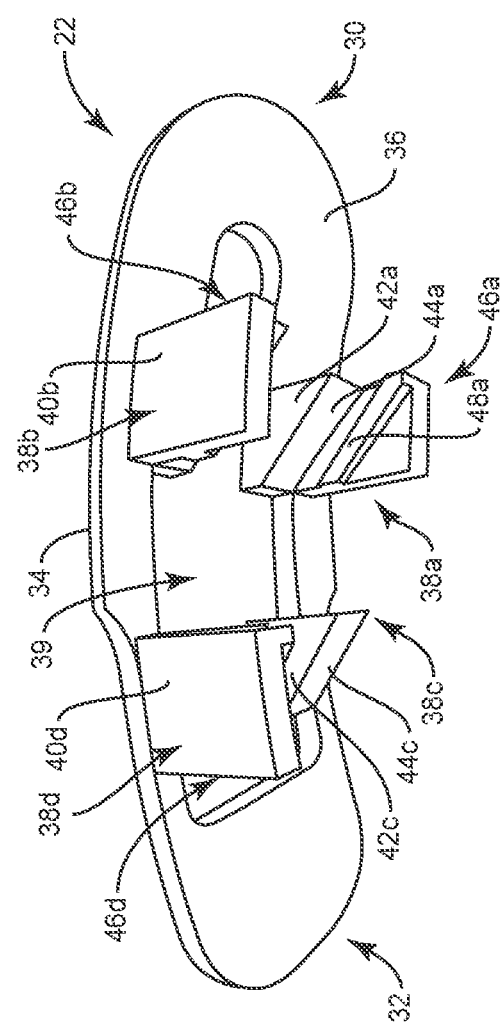
FIG. 6 is a bottom, perspective view of a component of the implant shown in FIG. 1.

Endplate 22 extends between an end 30 and an opposite end 32, as shown in FIGS. 5 and 6. Endplate 22 comprises an engagement surface 34 configured to engage a first vertebra and an inner surface 36 opposite engagement surface 34. Inner surface 36 faces away from engagement surface 34. End 30 of endplate 22 comprises a pair of spaced apart projections, such as, for example, tabs 38a, 38b that extend from inner surface 36, and end 32 of endplate 22 comprises a pair of spaced apart projections, such as, for example, tabs 38c, 38d that extend from inner surface 36. Tab 38a is spaced apart from tab 38b by an opening 39 that extends through engagement surface 34 and inner surface 36. Tab 38c is spaced apart from tab 38d by opening 39. In some embodiments, all or a portion of tab 38a extends parallel to tab 38b along arc X and all or a portion of tab 38c extends parallel to tab 38d along arc X. In some embodiments, tab 38a, tab 38b, tab 38c and/or tab 38d may be disposed at alternate orientations, relative to arc X, such as, for example, parallel, transverse, perpendicular and/or other angular orientations such as acute or obtuse, co-axial and/or may be offset or staggered.

Tab 38a comprises a planar outer surface 40a, an opposite inner surface 42a and an inclined surface, such as, for example, a ramp 44a positioned between outer and inner surfaces 40a, 42a. Tab 38b comprises a planar outer surface 40b, an opposite inner surface 42b and an inclined surface, such as, for example, a ramp 44b positioned between outer and inner surfaces 40b, 42b. Tab 38c comprises a planar outer surface 40c, an opposite inner surface 42c and an inclined surface, such as, for example, a ramp 44c positioned between outer and inner surfaces 40c, 42c. Tab 38d comprises a planar outer surface 40d, an opposite inner surface 42d and an inclined surface, such as, for example, a ramp 44d positioned between outer and inner surfaces 40d, 42d. Inner surface 42a faces inner surface 42b and inner surface 42c faces inner surface 42d. Ramps 44a, 44b, 44c, 44d are configured to slidably engage ramps of wedge 26 to move implant 20 between the undeployed or unexpanded configuration, shown in FIGS. 1 and 2, and the deployed or expanded configuration, shown in FIGS. 3 and 4, as discussed herein. It is envisioned that endplate 22 can include any number of ramps, in addition to ramps 44a, 44b, 44c, 44d. In some embodiments, endplate 22 comprises an even number of ramps. In some embodiments, endplate 22 comprises an odd number of ramps, Ramps 44a, 44b, 44c, 44d each extend transverse to engagement surface 34 and/or inner surface 36. In some embodiments, ramps 44a, 44b, 44c, 44d each extend at an acute angle relative to engagement surface 34 and/or inner surface 36. In some embodiments, ramps 44a, 44b, 44c, 44d each extend at the same angle relative to engagement surface 34 and/or inner surface 36. In some embodiments, ramps 44a, 44b each extend at a first angle relative to engagement surface 34 and/or inner surface 36 and ramps 44c, 44d each extend at a second angle relative to engagement surface 34 and/or inner surface 36, the first angle being different than the second angle. In some embodiments, ramps 44a, 44b, 44c, 44d extend at different angles relative to engagement surface 34 and/or inner surface 36. In some embodiments, ramp 44a, ramp 44b, ramp 44c and/or ramp 44d may be disposed at alternate orientations, relative to engagement surface 34 and/or inner surface 36, such as, for example, transverse and/or other angular orientations such as acute or obtuse, and/or may be offset or staggered.

In some embodiments, ramps 44a, 44b, 44c, 44d define di almost surfaces of tabs 38a, 38b, 38c, 38d, respectively. That is, tabs 38a, 38b, 38c, 38d do not extend distally beyond ramps 44a, 44b, 44c, 44d. In some embodiments, at least one of tabs 38a, 38b, 38c, 38d includes an extension that extends distally from at least one of ramps 44a, 44b, 44c, 44d. For example, tab 44a includes an extension 46a that extends distally from ramp 44a. Extension 46a includes an outer surface that is flush with outer surface 40a and an opposite inner surface. Extension 46a includes a supplemental ramp, such as, for example, an outrigger 48a that extends outwardly from the inner surface of extension 46a. Tab 44b includes an extension 46b that extends distally from ramp 44b. Extension 46b includes an outer surface that is flush with outer surface 40b and an opposite inner surface. Extension 46b includes a supplemental ramp, such as, for example, an outrigger 48b that extends outwardly from the inner surface of extension 46b. Tab 44d includes an extension 46d that extends distally from ramp 44d. Extension 46d includes an outer surface that is flush with outer surface 40d and an opposite inner surface. Extension 46d includes a supplemental ramp, such as, for example, an outrigger 48d that extends outwardly from the inner surface of extension 46d. Outriggers 48a, 48b, 48d are configured to be slidably disposed in grooves in wedge 26 as ramps 44a, 44b, 44c, 44d translate along the ramps of wedge 26 as implant 20 moves between the undeployed or unexpanded configuration, shown in FIGS. 1 and 2, and the deployed or expanded configuration, shown in FIGS. 3 and 4, as discussed herein. In some embodiments, outriggers 48a, 48b, 48d extend parallel to ramps 44a, 44b, 44d, respectively. In some embodiments, outriggers 48a, 48b, 48d extend transverse to ramps 44a, 44b, 44d, respectively. In some embodiments, outrigger 48a, outrigger 48b and/or outrigger 48d may be disposed at alternate orientations, relative to engagement surface 34 and/or inner surface 36, such as, for example, transverse and/or other angular orientations such as acute or obtuse, and/or may be offset or staggered.

In some embodiments, engagement surface 34 is smooth. That is, engagement surface 34 is free of any recesses or protrusions. In some embodiments, engagement surface 34 is textured and includes a plurality of projections 34a, as shown in FIG. 2, for example. Projections 34a are spaced apart from one another by gaps 34b. In some embodiments, engagement surface 34 includes one or a plurality of rows of projections 34a. In some embodiments, projections 34a each include a planar upper surface that extends parallel to inner surface 36 of endplate 22. In some embodiments, projections 34a each have a square configuration. In some embodiments, projections 34a may be variously shaped, such as, for example, oval, oblong, triangular, square, polygonal, irregular, uniform, non-uniform, offset, staggered, undulating, arcuate, variable and/or tapered.

Figure 7:
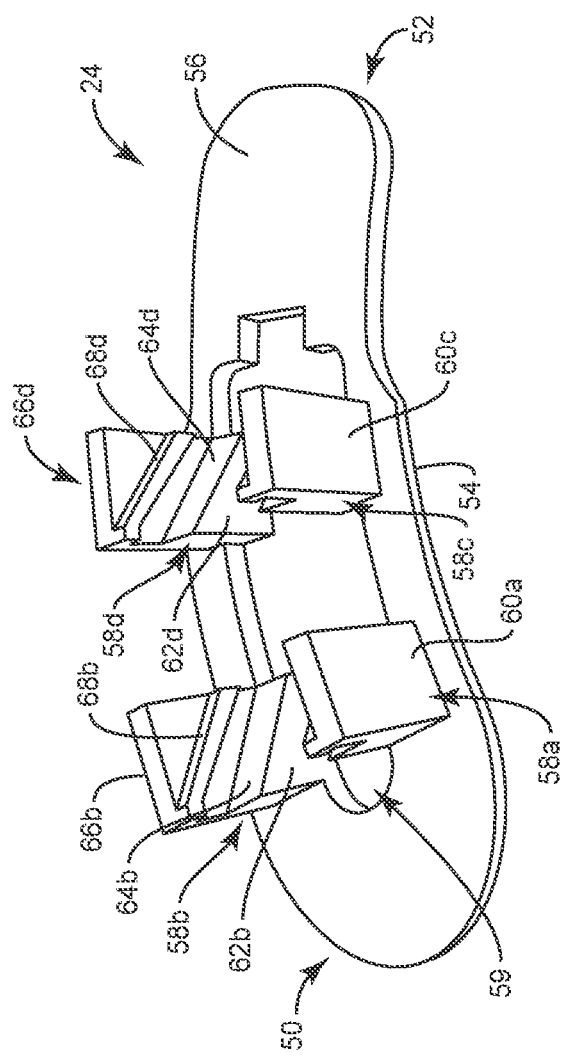
FIG. 7 is a top, perspective view of a component of the implant shown in FIG. 1.
Figure 8:
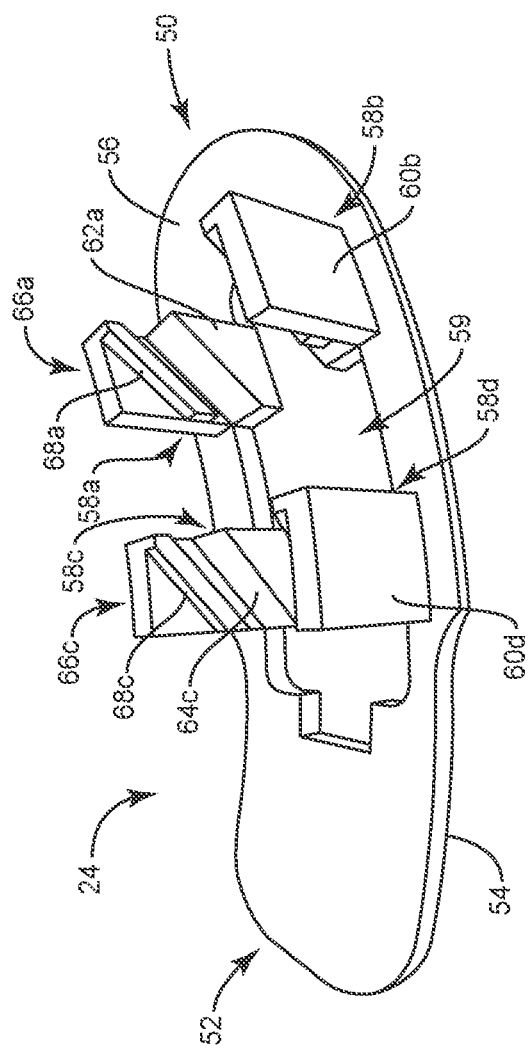
FIG. 8 is a top, perspective view of a component of the implant shown in FIG. 1.

Endplate 24 is similar to endplate 22. Endplate 24 extends between an end 50 and an opposite end 52, as shown in FIGS. 7 and 8. When endplates 22, 24 are positioned within frame 28, end 30 of endplate 22 is positioned adjacent to end 50 of endplate 24 and end 32 of endplate 22 is positioned adjacent to end 52 of endplate 24. Endplate 24 comprises an engagement surface 54 configured to engage a second vertebra that is adjacent to the first vertebra and an inner surface 56 opposite engagement surface 54. The first and second vertebrae define an intervertebral disc space therebetween. Inner surface 56 of endplate 24 faces inner surface 36 of endplate 22 and faces away from engagement surface 54. End 50 of endplate 24 comprises a pair of spaced apart projections, such as, for example, tabs 58a, 58b that extend from inner surface 56, and end 52 of endplate 24 comprises a pair of spaced apart projections, such as, for example, tabs 58c, 58d that extend from inner surface 36. Tab 58a is spaced apart from tab 58b by an opening 59 that extends through engagement surface 54 and inner surface 56. Tab 58c is spaced apart from tab 58d by opening 59. In some embodiments, all or a portion of tab 58a extends parallel to tab 58b along arc X and all or a portion of tab 58c extends parallel to tab 58d along arc X. In some embodiments, tab 58a, tab 58b, tab 58c and/or tab 58d may be disposed at alternate orientations, relative to arc X, such as, for example, parallel, transverse, perpendicular and/or other angular orientations such as acute or obtuse, co-axial and/or may be offset or staggered.

Tab 58a comprises a planar outer surface 60a, an opposite inner surface 62a and an inclined surface, such as, for example, a ramp 64a positioned between outer and inner surfaces 60a, 62a. Tab 58b comprises a planar outer surface 60b, an opposite inner surface 62b and an inclined surface, such as, for example, a ramp 64b positioned between outer and inner surfaces 60b, 62b. Tab 58c comprises a planar outer surface 60c, an opposite inner surface 62c and an inclined surface, such as, for example, a ramp 64c positioned between outer and inner surfaces 60c, 62c. Tab 58d comprises a planar outer surface 60d, an opposite inner surface 62d and an inclined surface, such as, for example, a ramp 64d positioned between outer and inner surfaces 60d, 62d. Inner surface 62a faces inner surface 62b and inner surface 62c faces inner surface 62d. Ramps 64a, 64b, 64c, 64d are configured to slidably engage ramps of wedge 26 to move implant 20 between the undeployed or unexpanded configuration, shown in FIGS. 1 and 2, and the deployed or expanded configuration, shown in FIGS. 3 and 4, as discussed herein. It is envisioned that endplate 24 can include any number of ramps, in addition to ramps 64a, 64b, 64c, 64d. In some embodiments, endplate 24 comprises an even number of ramps. In some embodiments, endplate 24 comprises an odd number of ramps. In some embodiments, endplate 24 includes the same number of ramps as endplate 22. In some embodiments, endplate 24 includes more ramps than endplate 22. In some embodiments, endplate 24 includes fewer ramps than endplate 22.

Ramps 64a, 64b, 64c, 64d each extend transverse to engagement surface 54 and/or inner surface 56. In some embodiments, ramps 64a, 64b, 64c, 64d each extend at an acute angle relative to engagement surface 54 and/or inner surface 56. In some embodiments, ramps 64a, 64b, 64c, 64d each extend at the same angle relative to engagement surface 54 and/or inner surface 56. In some embodiments, ramps 64a, 64b each extend at a first angle relative to engagement surface 54 and/or inner surface 56 and ramps 64c, 64d each extend at a second angle relative to engagement surface 54 and/or inner surface 56, the first angle being different than the second angle. In some embodiments, ramps 64a, 64b, 64c, 64d extend at different angles relative to engagement surface 54 and/or inner surface 56. In some embodiments, ramp 64a, ramp 64b, ramp 64c and/or ramp 64d may be disposed at alternate orientations, relative to engagement surface 54 and/or inner surface 56, such as, for example, transverse and/or other angular orientations such as acute or obtuse, and/or may be offset or staggered.

In some embodiments, ramps 64a, 64b, 64c, 64d define proximalmost surfaces of tabs 58a, 58b, 58c, 58d, respectively. That is, tabs 58a, 58b, 58c, 58d do not extend proximally beyond ramps 64a, 64b, 64c, 64d. In some embodiments, at least one of tabs 58a, 58b, 58c, 58d includes an extension that extends distally from at least one of ramps 64a, 64b, 64c, 64d. For example, tab 64a includes an extension 66a that extends proximally from ramp 44a. Extension 66a includes an outer surface that is flush with outer surface 60a and an opposite inner surface. Extension 66a includes a supplemental ramp, such as, for example, an outrigger 68a that extends outwardly from the inner surface of extension 66a. Tab 64b includes an extension 66b that extends proximally from ramp 64b. Extension 66b includes an outer surface that is flush with outer surface 60b and an opposite inner surface. Extension 66b includes a supplemental ramp, such as, for example, an outrigger 68b that extends outwardly from the inner surface of extension 66b. Tab 64c includes an extension 66c that extends proximally from ramp 64c. Extension 66c includes an outer surface that is flush with outer surface 60c and an opposite inner surface. Extension 66c includes a supplemental ramp, such as, for example, an outrigger 68c that extends outwardly from the inner surface of extension 66c. Tab 64d includes an extension 66d that extends proximally from ramp 64d. Extension 66d includes an outer surface that is flush with outer surface 60d and an opposite inner surface. Extension 66d includes a supplemental ramp, such as, for example, an outrigger 68d that extends outwardly from the inner surface of extension 66d. Outriggers 68a, 68b, 68c, 68d are configured to be slidably disposed in grooves in wedge 26 as ramps 64a, 64b, 64c, 64d translate along the ramps of wedge 26 as implant 20 moves between the undeployed or unexpanded configuration, shown in FIGS. 1 and 2, and the deployed or expanded configuration, shown in FIGS. 3 and 4, as discussed herein. In some embodiments, outriggers 68a, 68b, 68c, 68d extend parallel to ramps 64a, 64b, 64c, 64d, respectively. In some embodiments, outriggers 68a, 68b, 68c, 68d extend transverse to ramps 64a, 64b, 64c, 64d, respectively. In some embodiments, outrigger 68a, outrigger 68b, outrigger 68c and/or outrigger 68d may be disposed at alternate orientations, relative to engagement surface 54 and/or inner surface 56, such as, for example, transverse and/or other angular orientations such as acute or obtuse, and/or may be offset or staggered.

In some embodiments, engagement surface 54 is smooth. That is, engagement surface 54 is free of any recesses or protrusions. In some embodiments, engagement surface 54 is textured and includes a plurality of projections, similar or identical to projections 34a. The projections of engagement surface 54 are spaced apart from one another by gaps similar or identical to gaps 34b. In some embodiments, engagement surface 54 includes one or a plurality of rows of projections. In some embodiments, the projections of engagement surface 54 each include a planar upper surface that extends parallel to inner surface 56 of endplate 24. In some embodiments, the projections of engagement surface 54 each have a square configuration. In some embodiments, the projections of engagement surface 54 may be variously shaped, such as, for example, oval, oblong, triangular, square, polygonal, irregular, uniform, non-uniform, offset, staggered, undulating, arcuate, variable and/or tapered.

Figure 9:
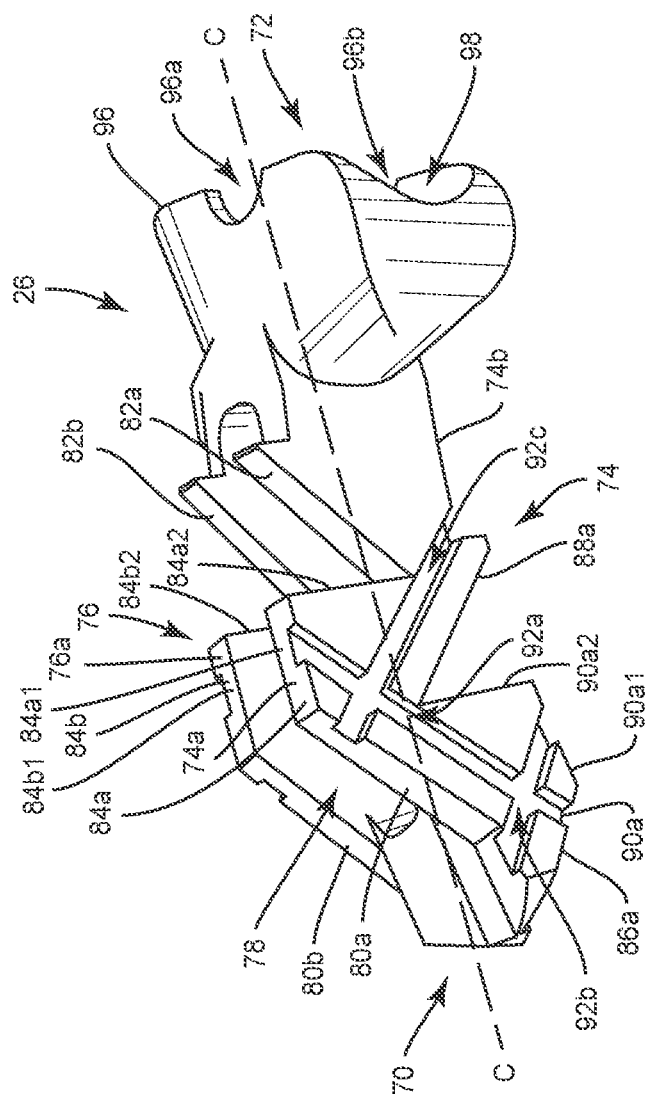
FIG. 9 is a side, perspective view of a component of the implant shown in FIG. 1.
Figure 10:
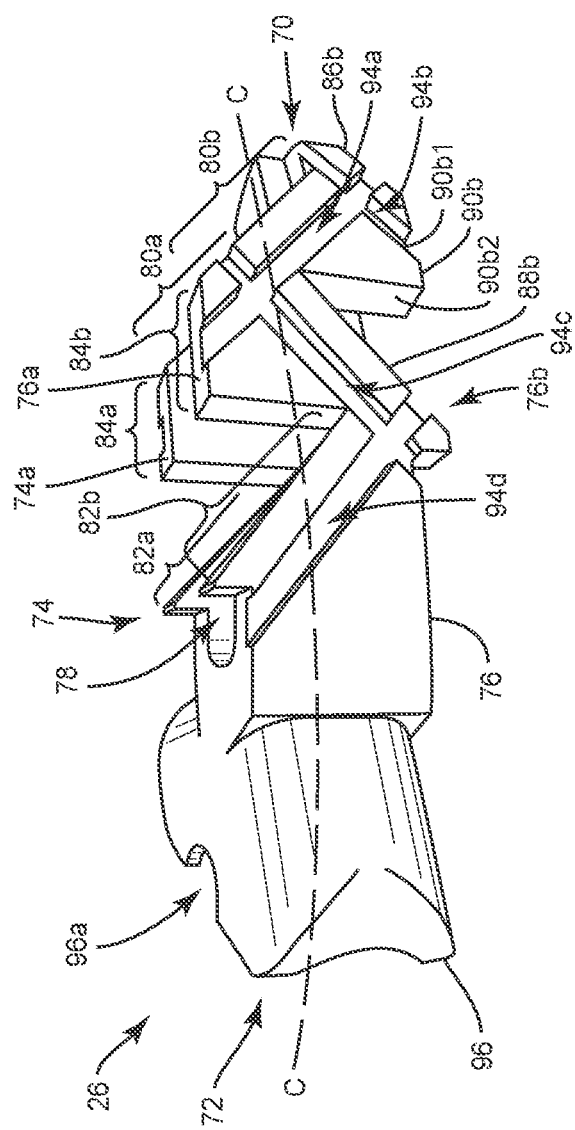
FIG. 10 is a side, perspective view of a component of he implant shown in FIG. 1.
Figure 11:
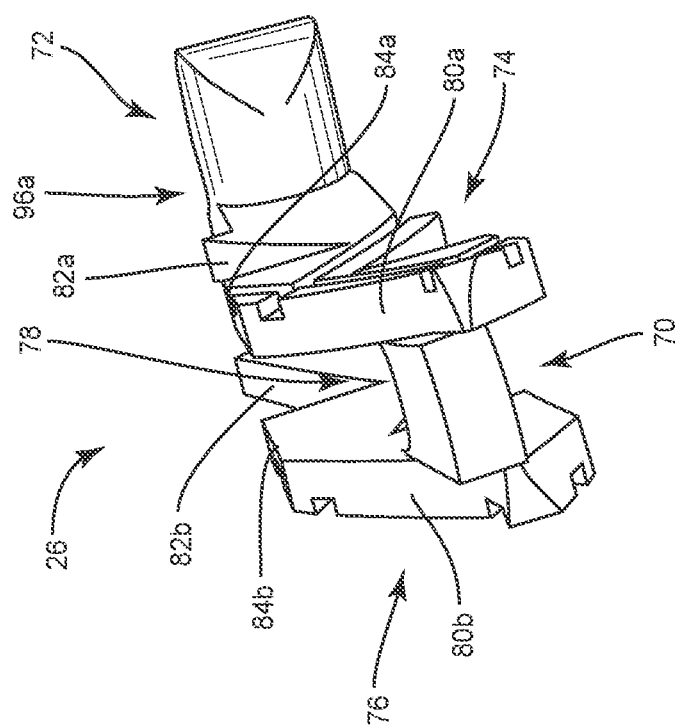
FIG. 11 is an end, perspective view of a component of the implant shown in FIG. 1.

Wedge 26 extends between an end 70 and an opposite end 72, as shown in FIGS. 9-12. End 70 of wedge 26 is positioned adjacent to end 30 of endplate 22 and end 50 of endplate 24, and end 72 is positioned adjacent to end 32 of endplate 22 and end 52 of endplate 24 when endplates 22, 24 and wedge 26 are positioned within frame 28. Wedge 26 comprises a sidewall 74, and a sidewall 76 opposite sidewall 74. Sidewall 76 is spaced apart from sidewall 74 by ends 70, 72. Sidewalls 74, 76 each extend from end 70 to end 72 to connect ends 70, 72. In some embodiments, all or a portion of sidewall 74 extends parallel to sidewall 76 along arc X. In some embodiments, all or a portion of sidewall 74 and/or sidewall 76 may be disposed at alternate orientations, relative to arc X, such as, for example, parallel, transverse, perpendicular and/or other angular orientations such as acute or obtuse, co-axial and/or may be offset or staggered. Inner surfaces of ends 70, 72 and sidewalls 74, 76 define a cavity 78 that extends through upper surfaces 74*a*, 76*a* of sidewalls 74, 76 and lower surfaces 74*b*, 76*b* of sidewalls 74, 76. A maximum distance between upper and lower surfaces 74*a*, 74*b* of sidewall 74 and/or between upper and lower surfaces 76*a*, 76*b* of sidewall 76 define a maximum height of wedge 26. Wedge 26 comprises a centerline C that is positioned equidistant between upper and lower surfaces 74*a*, 74*b* and equidistant between upper and lower surfaces 76*a*, 76*b*, as shown in FIGS. 9 and 10. That is, centerline C is equidistant between upper and lower surfaces 74*a*, 74*b* that define the maximum height of wedge 26 and equidistant between upper and lower surfaces 76*a*, 76*b* that define the maximum height of wedge 26. Sidewall 74 is spaced apart from sidewall 76 by cavity 78. Cavity 78 is in communication with openings 39, 59 of endplates 22, 24 such that a material, such as, for example, bone graft can be inserted through one of openings 39, 59 and into cavity 78 of wedge 26, as discussed herein.

Upper surface 74*a* of sidewall 74 defines a mating part, such as, for example, a ramp 80*a*, a mating part, such as, for example, a ramp 82*a* and a section 84*a* positioned between ramps 80*a*, 82*a*. Upper surface 76*a* of sidewall 76 defines a mating part, such as, for example, a ramp 80*b*, a mating part, such as, for example, a ramp 82*b* and a section 84*b* positioned between ramps 80*b*, 82*b*. Ramps 80*a*, 80*b*, 82*a*, 82*b* each extend from uppermost portions of upper surfaces 74*a*, 76*a* and through centerline C. That is, ramps 80*a*, 80*b*, 82*a*, 82*b* each extend beyond centerline C. Ramps 80*a*, 80*b*, 82*a*, 82*b* each extend transverse to centerline C, engagement surfaces 34, 54 and/or inner surfaces 36, 56. In some embodiments, ramps 80*a*, 80*b*, 82*a*, 82*b* each extend at an acute angle relative to centerline C, engagement surfaces 34, 54 and/or inner surfaces 36, 56. In some embodiments, ramps 80*a*, 80*b*, 82*a*, 82*b* each extend at the same angle relative to centerline C, engagement surfaces 34, 54 and/or inner surfaces 36, 56. In some embodiments, ramps 80*a*, 80*b* each extend at a first angle relative to centerline C, engagement surfaces 34, 54 and/or inner surfaces 36, 56, and ramps 82*a*, 82*b* each extend at a second angle relative to centerline C, engagement surfaces 34, 54 and/or inner surfaces 36, 56, the first angle being different than the second angle. In some embodiments, ramps 80*a*, 80*b*, 82*a*, 82*b* extend at different angles relative to centerline C, engagement surfaces 34, 54 and/or inner surfaces 36, 56. In some embodiments, ramp 80*a*, ramp 80*b*, ramp 82*a* and/or ramp 82*b* may be disposed at alternate orientations, relative to centerline C, engagement surfaces 34, 54 and/or inner surfaces 36, 56, such as, for example, transverse and/or other angular orientations such as acute or obtuse, and/or may be offset or staggered. It is envisioned that the upper surfaces of sidewalls 74, 76 can include any number of ramps, in addition to ramps 80*a*, 80*b*, 82*a*, 82*b*. In some embodiments, the upper surfaces of sidewalls 74, 76 comprise an even number of ramps. In some embodiments, the upper surfaces of sidewalls 74, 76 comprise an odd number of ramps. In some embodiments, the upper surfaces of sidewalls 74, 76 include the same number of ramps as endplate 22. In some embodiments, endplate 22 includes more ramps than the upper surfaces of sidewalls 74, 76. In some embodiments, endplate 22 includes fewer ramps than the upper surfaces of sidewalls 74, 76.

Figure 3:
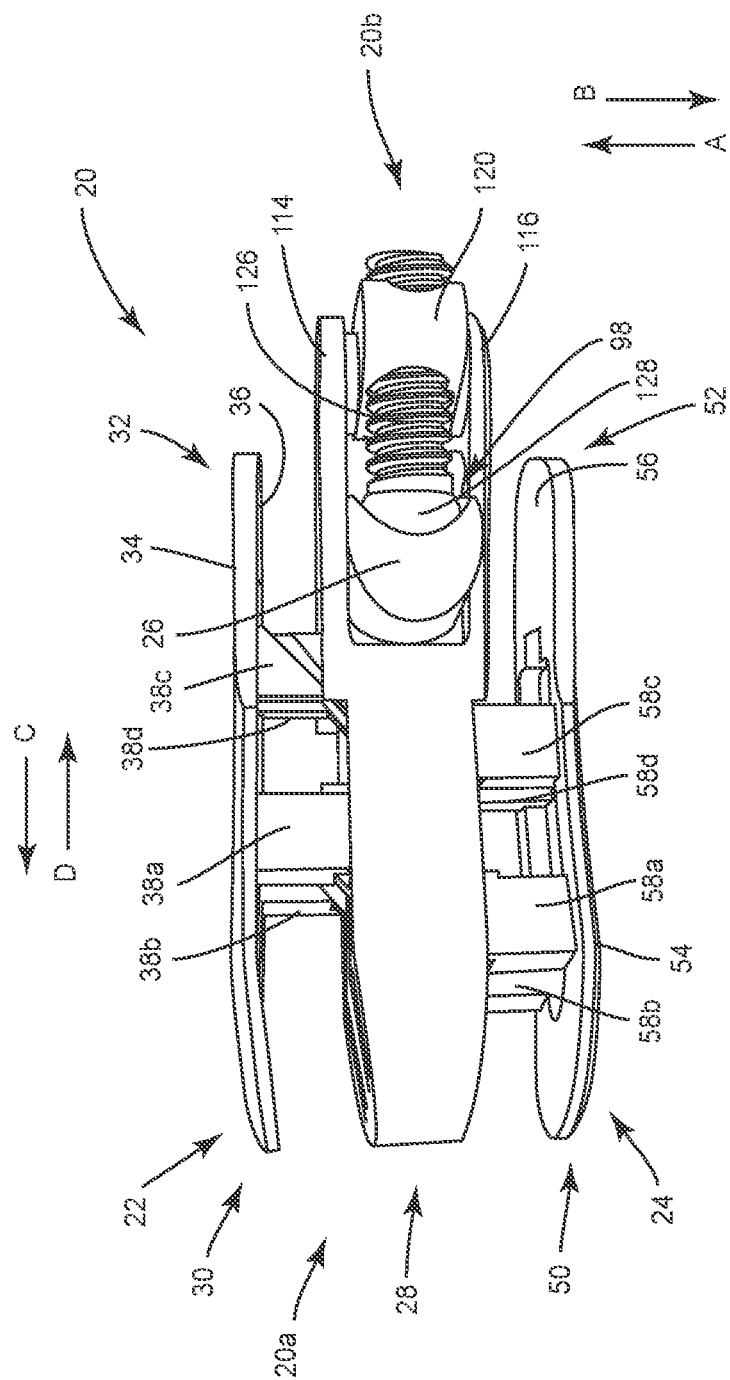
FIG. 3 is a side view of the implant shown in FIG. 1.
Figure 4:
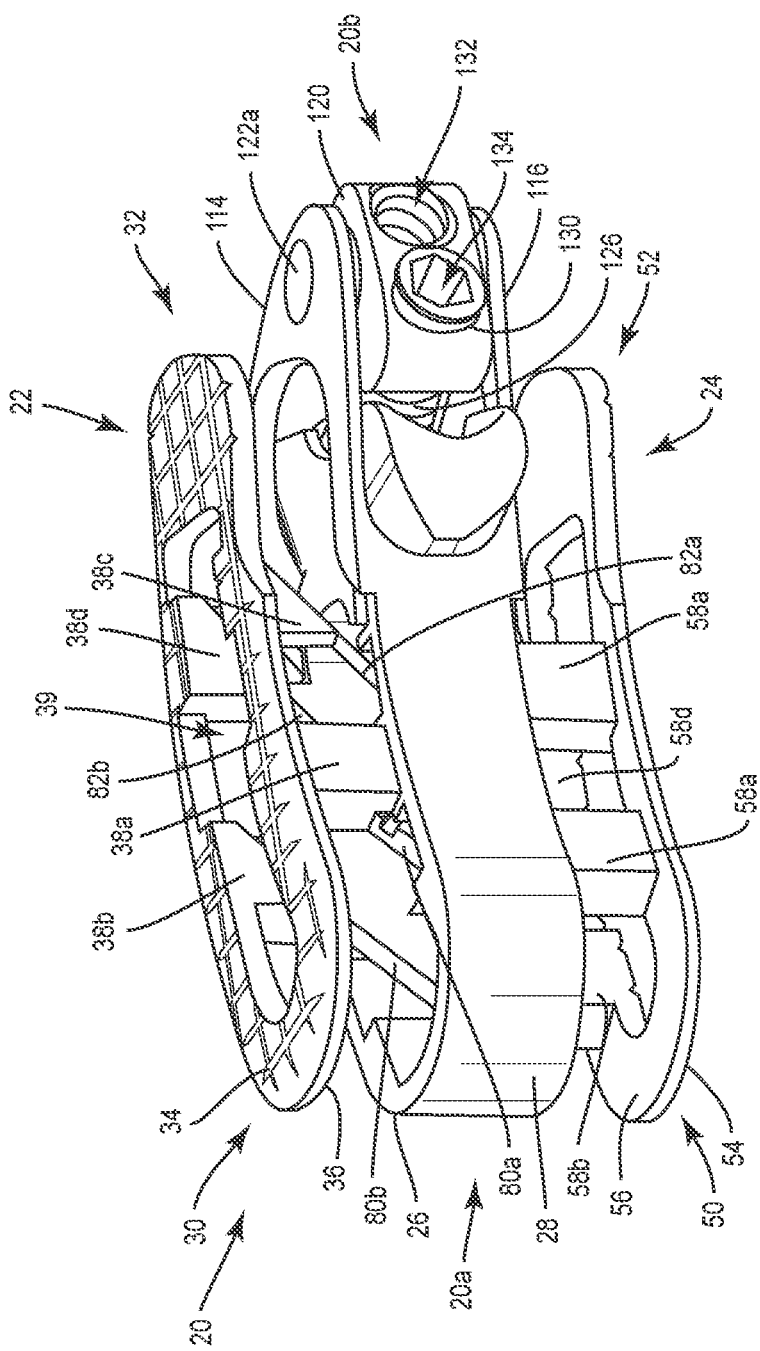
FIG. 4 is a perspective view of the implant shown in FIG. 1.

Ramp 44*a* engages and translates along ramp 80*a* as implant 20 moves between the undeployed or unexpanded configuration, shown in FIGS. 1 and 2, and the deployed or expanded configuration, shown in FIGS. 3 and 4; ramp 44*b* engages and translates along ramp 80*b* as implant 20 moves between the undeployed or unexpanded configuration and the deployed or expanded configuration; ramp 44*c* engages and translates along ramp 82*a* as implant 20 moves between the undeployed or unexpanded configuration and the deployed or expanded configuration; and ramp 44*d* engages and translates along ramp 82*b* as implant 20 moves between the undeployed or unexpanded configuration and the deployed or expanded configuration, as discussed herein.

Ramp 80*a* is spaced apart from ramp 82*a* by section 84*a*. Section 84*a* comprises a first portion 84*a*1 that extends parallel to centerline C, engagement surfaces 34, 54 and/or inner surfaces 36, 56, and a second portion 84*a*2 that extends perpendicular to centerline C, engagement surfaces 34, 54 and/or inner surfaces 36, 56. Ramp 80*a* extends from portion 84*a*1 and ramp 82*a* extends from portion 84*a*2. Ramp 80*b* is spaced apart from ramp 82*b* by section 84*b*. Section 84*b* comprises a first portion 84*b*1 that extends parallel to centerline C, engagement surfaces 34, 54 and/or inner surfaces 36, 56 and a second portion 84*b*2 that extends perpendicular to centerline C, engagement surfaces 34, 54 and/or inner surfaces 36, 56. Ramp 80*b* extends from portion 84*b*1 and ramp 82*b* extends from portion 84*b*2. In some embodiments, portion 84*a*1, 84*a*2, 84*b*1 and/or portion 84*b*2 may be disposed at alternate orientations, relative to centerline C, engagement surfaces 34, 54 and/or inner surfaces 36, 56, such as, for example, parallel, transverse, perpendicular and/or other angular orientations such as acute or obtuse, and/or may be offset or staggered.

Lower surface 74*b* of sidewall 74 defines a mating part, such as, for example, a ramp 86*a*, a mating part, such as, for example, a ramp 88*a* and a section 90*a* positioned between ramps 86*a*, 88*a*. Lower surface 76*b* of sidewall 76 defines a mating part, such as, for example, a ramp 86*b*, a mating part, such as, for example, a ramp 88*b* and a section 90*b* positioned between ramps 86*b*, 88*b*. Ramps 86*a*, 86*b*, 88*a*, 88*b* each extend from lowermost portions of lower surfaces 74*b*, 76*b* and through centerline C. That is, ramps 86*a*, 86*b*, 88*a*, 88*b* each extend beyond centerline C. Ramps 86*a*, 86*b*, 88*a*, 88*b* each extend transverse to centerline C, engagement surfaces 34, 54 and/or inner surfaces 36, 56. In some embodiments, ramps 86*a*, 86*b*, 88*a*, 88*b* each extend at an acute angle relative to centerline C, engagement surfaces 34, 54 and/or inner surfaces 36, 56. In some embodiments, ramps 86*a*, 86*b*, 88*a*, 88*b* each extend at the same angle relative to centerline C, engagement surfaces 34, 54 and/or inner surfaces 36, 56. In some embodiments, ramps 86*a*, 86*b* each extend at a first angle relative to centerline C, engagement surfaces 34, 54 and/or inner surfaces 36, 56 and ramps 88a, 88b each extend at a second angle relative to centerline C, engagement surfaces 34, 54 and/or inner surfaces 36, 56, the first angle being different than the second angle. In some embodiments, ramps 86a, 86b, 88a, 88b extend at different angles relative to centerline C, engagement surfaces 34, 54 and/or inner surfaces 36, 56. In some embodiments, ramp 86a, ramp 86b, ramp 88a and/or ramp 88b may be disposed at alternate orientations, relative to centerline C, engagement surfaces 34, 54 and/or inner surfaces 36, 56, such as, for example, transverse and/or other angular orientations such as acute or obtuse, and/or may be offset or staggered. It is envisioned that the lower surfaces of sidewalls 74, 76 can include any number of ramps, in addition to ramps 86a, 86b, 88a, 88b. In some embodiments, the lower surfaces of sidewalls 74, 76 comprise an even number of ramps. In some embodiments, the lower surfaces of sidewalls 74, 76 comprise an odd number of ramps. In some embodiments, the lower surfaces of sidewalls 74, 76 include the same number of ramps as endplate 24. In some embodiments, endplate 24 includes more ramps than the lower surfaces of sidewalls 74, 76. In some embodiments, endplate 24 includes fewer ramps than the lower surfaces of sidewalls 74, 76.

Ramps 80a, 80b are positioned between ramps 86a, 86b and ramps 88a, 88b along the length of wedge 26, and ramps 88a, 88b are positioned between ramps 80a, 80b and ramps 82a, 82b along the length of wedge 26. Ramp 64a engages and translates along ramp 86a as implant 20 moves between the undeployed or unexpanded configuration, shown in FIGS. 1 and 2, and the deployed or expanded configuration, shown in FIGS. 3 and 4; ramp 64b engages and translates along ramp 86b as implant 20 moves between the undeployed or unexpanded configuration and the deployed or expanded configuration; ramp 64c engages and translates along ramp 88a as implant 20 moves between the undeployed or unexpanded configuration and the deployed or expanded configuration; ramp 64d engages and translates along ramp 88b as implant 20 moves between the undeployed or unexpanded configuration and the deployed or expanded configuration, as discussed herein.

Ramp 86a is spaced apart from ramp 88a by section 90a. Section 90a comprises a first portion 90a1 that extends parallel to centerline C, engagement surfaces 34, 54 and/or inner surfaces 36, 56, and a second portion 90a2 that extends perpendicular to centerline C, engagement surfaces 34, 54 and/or inner surfaces 36, 56. Ramp 86a extends from portion 90a1 and ramp 88a extends from portion 90a2. Ramp 86b is spaced apart from ramp 88b by section 90b. Section 90b comprises a first portion 90b1 that extends parallel to centerline C, engagement surfaces 34, 54 and/or inner surfaces 36, 56, and a second portion 90b2 that extends perpendicular to centerline C, engagement surfaces 34, 54 and/or inner surfaces 36, 56. Ramp 86b extends from portion 90b1 and ramp 88b extends from portion 90b2. In some embodiments, portion 90a1, 90a2, 90b1 and/or portion 90b2 may be disposed at alternate orientations, relative to centerline C, engagement surfaces 34, 54 and/or inner surfaces 36, 56, such as, for example, parallel, transverse, perpendicular and/or other angular orientations such as acute or obtuse, and/or may be offset or staggered.

An outer surface of sidewall 74 comprises a groove 92a that extends through ramp 86a and portion 84a1, a groove 92b that extends through portion 90a1 and a groove 92c that extends through ramp 80a. Groove 92a extends parallel to ramp 80a, groove 92b extends parallel to ramp 86a and groove 92c extends parallel to ramp 88a. Groove 92a extends through each of grooves 92b, 92c, as shown in FIG. 9. An outer surface of sidewall 76 comprises a groove 94a that extends through ramp 86b and portion 84b1, a groove 94b that extends through portion 90b1, a groove 94c that extends through ramp 80b and a groove 94d that extends through ramp 88b. Groove 94a extends parallel to ramp 80b, groove 94b extends parallel to ramp 86b, groove 94c extends parallel to ramp 88b and groove 94d extends parallel to ramp 82b. Groove 94a extends through each of grooves 94b, 94c, and groove 94d extends through groove 94c, as shown in FIG. 10.

Outrigger 48a is disposed in groove 92a and translates within groove 92a as implant 20 moves between the undeployed or unexpanded configuration, shown in FIGS. 1 and 2, and the deployed or expanded configuration, shown in FIGS. 3 and 4. Outrigger 48b is disposed within groove 94a and translates within groove 94a as implant 20 moves between the undeployed or unexpanded configuration and the deployed or expanded configuration. Outrigger 48d is disposed within groove 94d and translates within groove 94d as implant 20 moves between the undeployed or unexpanded configuration and the deployed or expanded configuration. Outrigger 68a is disposed within groove 92b and translates within groove 92b as implant 20 moves between the undeployed or unexpanded configuration and the deployed or expanded configuration. Outrigger 68b is disposed within groove 94b and translates within groove 94b as implant 20 moves between the undeployed or unexpanded configuration and the deployed or expanded configuration. Outrigger 68c is disposed within groove 92c and translates within groove 92c as implant 20 moves between the undeployed or unexpanded configuration and the deployed or expanded configuration. Outrigger 68d is disposed within groove 94c and translates within groove 94c as implant 20 moves between the undeployed or unexpanded configuration and the deployed or expanded configuration. Outriggers 48a, 48b, 48d, 68a, 68b, 68c, 68d are positioned in grooves 92a, 94a, 94d, 92b, 94b, 92c, 94c as ramps 44a, 44b, 44c, 44d translate along ramps 80a, 80b, 82a, 82b and ramps 64a, 64b, 64c, 64d translate along ramps 86a, 86b, 88a, 88b to add additional bearing area as well as an ability to close implant 20 when implant 20 is in the undeployed or unexpanded configuration, shown in FIGS. 1 and 2. That is, having outriggers 48a, 48b, 48d, 68a, 68b, 68c, 68d positioned in grooves 92a, 94a, 94d, 92b, 94b, 92c, 94c as ramps 44a, 44b, 44c, 44d translate along ramps 80a, 80b, 82a, 82b and ramps 64a, 64b, 64c, 64d translate along ramps 86a, 86b, 88a, 88b provides implant 20 with load bearing capabilities as implant 20 moves between the undeployed or unexpanded configuration and the deployed or expanded configuration, and when implant 20 is in the undeployed or unexpanded configuration and the deployed or expanded configuration.

Figure 12:
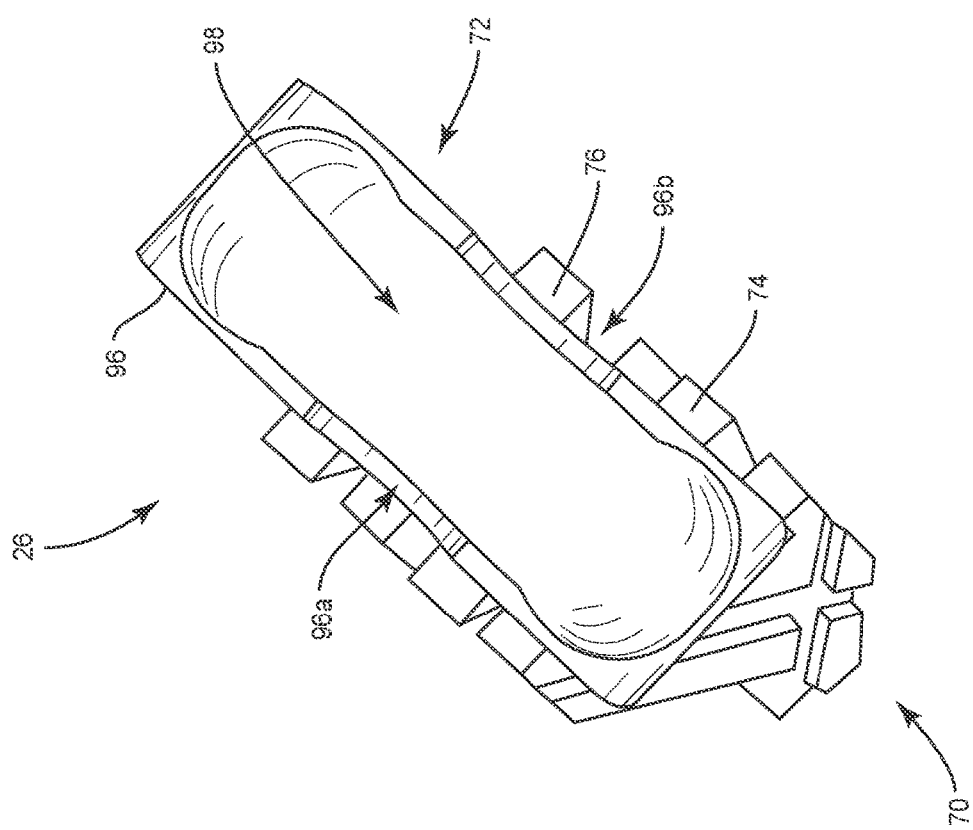
FIG. 12 is an end view of a component of the implant shown in FIG. 1.

End 72 of wedge 26 comprises an enlarged end wall 96, as shown in FIG. 12. Wall 96 has a maximum width that is greater than a maximum distance between the outer surface of sidewall 74 and the outer surface of sidewall 76. An inner surface of wall 96 defines an arcuate trough 98. Trough 98 is configured for disposal of an actuator of implant 20, as discussed herein. Trough 98 includes a first end adjacent to sidewall 74 and an opposite second end adjacent to sidewall 76. In some embodiments trough 98 has a continuous radius of curvature from the first end of trough 98 to the second end of trough 98. In some embodiments trough 98 has a variable radius of curvature from the first end of trough 98 to the second end of trough 98.

Wedge 26 may be broken into more than one piece such that the independent portions are separately controllable. In one embodiment, wedge 26 is broken into left and right halves which are controlled separately. In this configuration, projections 38a and 38c of endplate 22 and projections 58a and 58c of endplate 24 may be independently controlled from projections 38b and 38d of endplate 22 and projections 58b and 58d of endplate 24, in order to provide kyphosis or lordosis of the segment as needed. In one embodiment, wedge 26 is broken into front and back portions such that projections 38a and 38b of endplate 22 and projections 58a and 58b of endplate 24 may be controlled independently of projections 38c and 38d of endplate 22 and projections 58c and 58d of endplate 24, in order to provide coronal plane correction or manipulation.

In the accompanying Figures, the surfaces of ramps 44a-d of endplate 22, 64a-d of endplate 24 and 80a-b, and 82a-b of wedge 26 are illustrated as mating flat on flat. This configuration may provide a full sliding surface allowing one ramp to slide linearly relative to another ramp. However, it is contemplated that one or more of the surfaces may be arched or substantially arched in order to provide a point of contact between mating ramps. Such configuration would allow for a mating ramp to pivot or "rock" back and forth on the mating surface.

Figure 13:
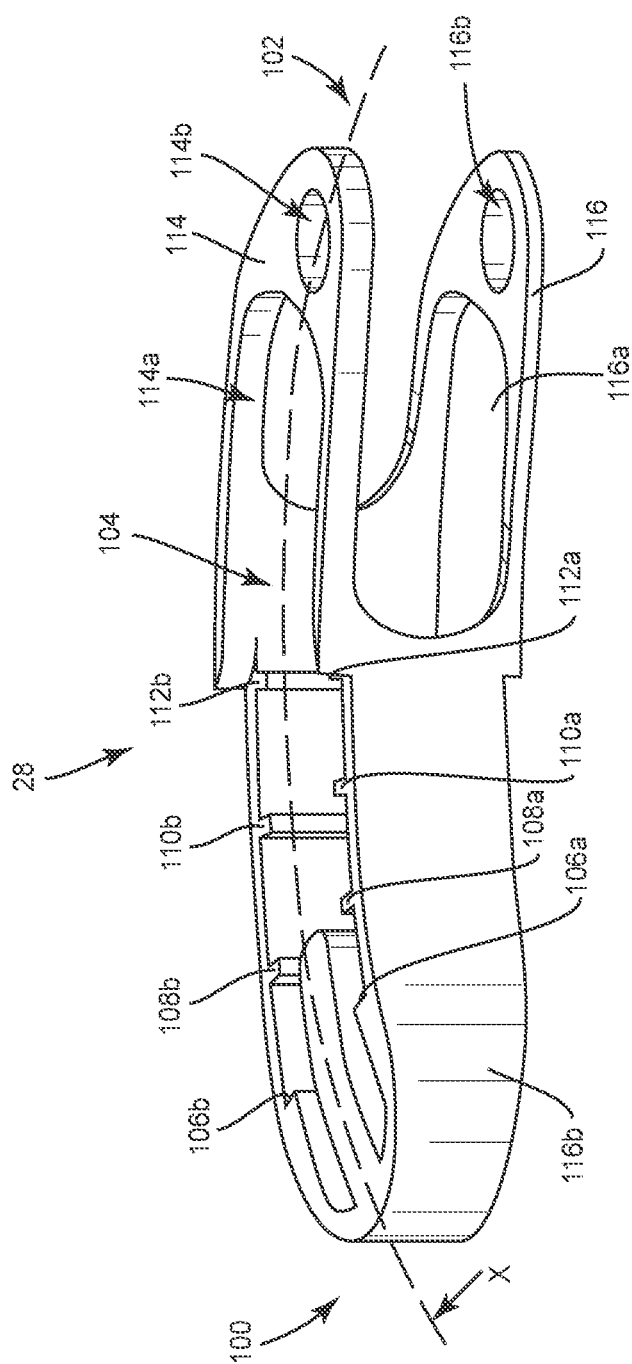
FIG. 13 is an end, perspective view of a component of the implant shown in FIG. 1.
Figure 14:
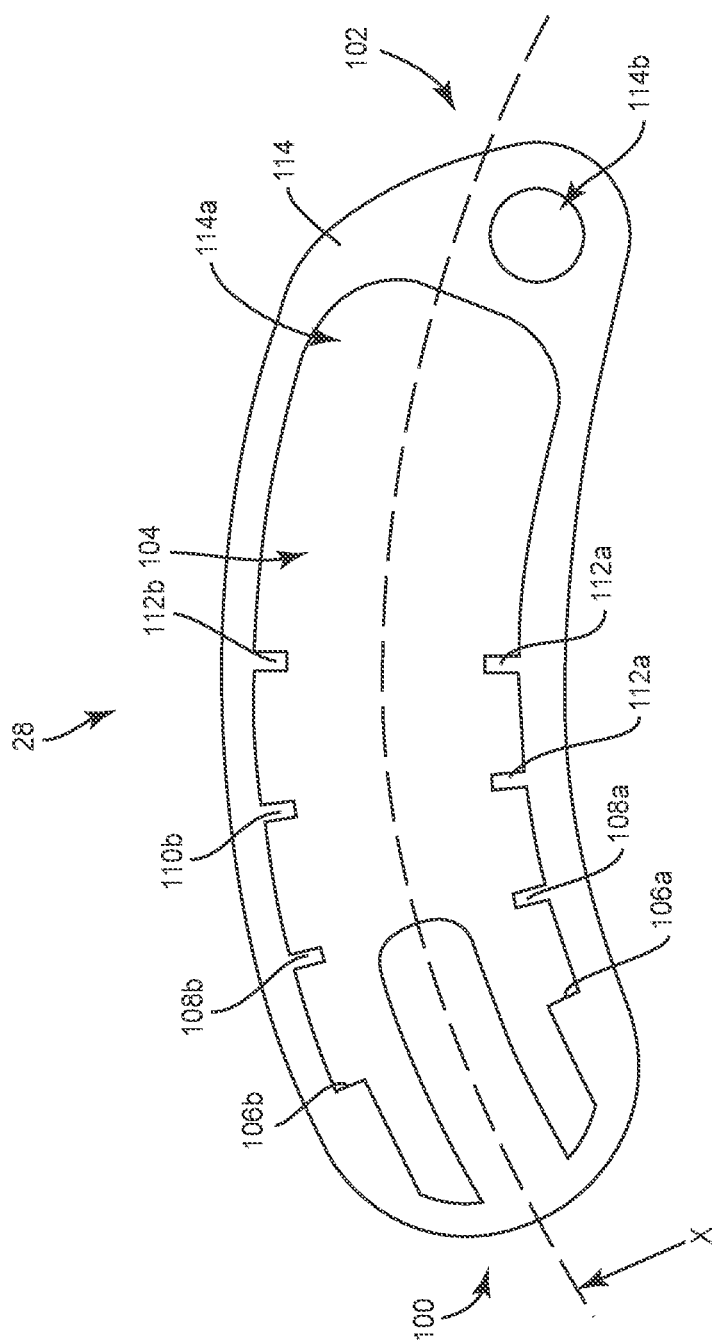
FIG. 14 is a top view of a component of the implant shown in FIG. 1.

Frame 28 extends between an end 100 and an opposite end 102, as shown in FIGS. 13 and 14. Frame 28 is curved along arc X between end 100 and end 102. Frame 28 includes an inner surface that defines an interior cavity 104. Wedge 26 and at least a portion of each of endplates 22, 24 are positioned within interior cavity 104. End 70 of wedge 26, end 30 of endplate 22 and end 50 of endplate 24 are positioned adjacent to end 100 of frame 28 when endplates 22, 24 and wedge 26 are positioned within interior cavity 104. End 72 of wedge 26, end 32 of endplate 22 and end 52 of endplate 24 are positioned adjacent to end 102 of frame 28 when endplates 22, 24 and wedge 26 are positioned within interior cavity 104.

Frame 28 includes a pair of flanges, 106a, 106b, a first pair of rails 108a, 108b, a second pair of rails 110a, 110b and a third pair of rails 112a, 112b. Flange 106a extends parallel to flange 106b. In some embodiments, flange 106a is coaxial with flange 106b. Rail 108a faces rail 108b; rail 110a faces rail 110b; and rail 112a faces rail 112b. Rail 108a is positioned between flange 106a and rail 110a; rail 108b is positioned between flange 106b and rail 110b; rail 110a is positioned between rail 108a and rail 112a; and rail 110b is positioned between rail 108b and rail 112b.

Figure 15:
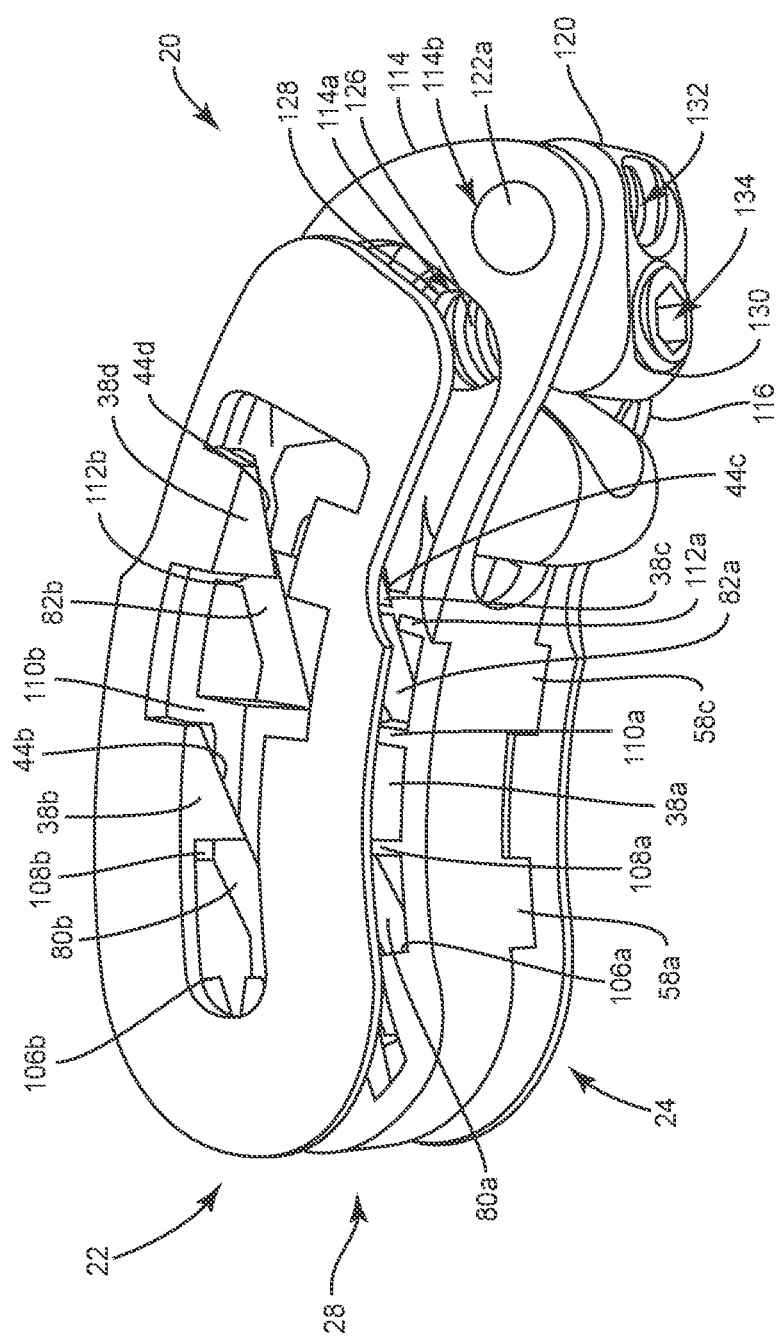
FIG. 15 is a top, perspective view of the implant shown in FIG. 1.
Figure 16:
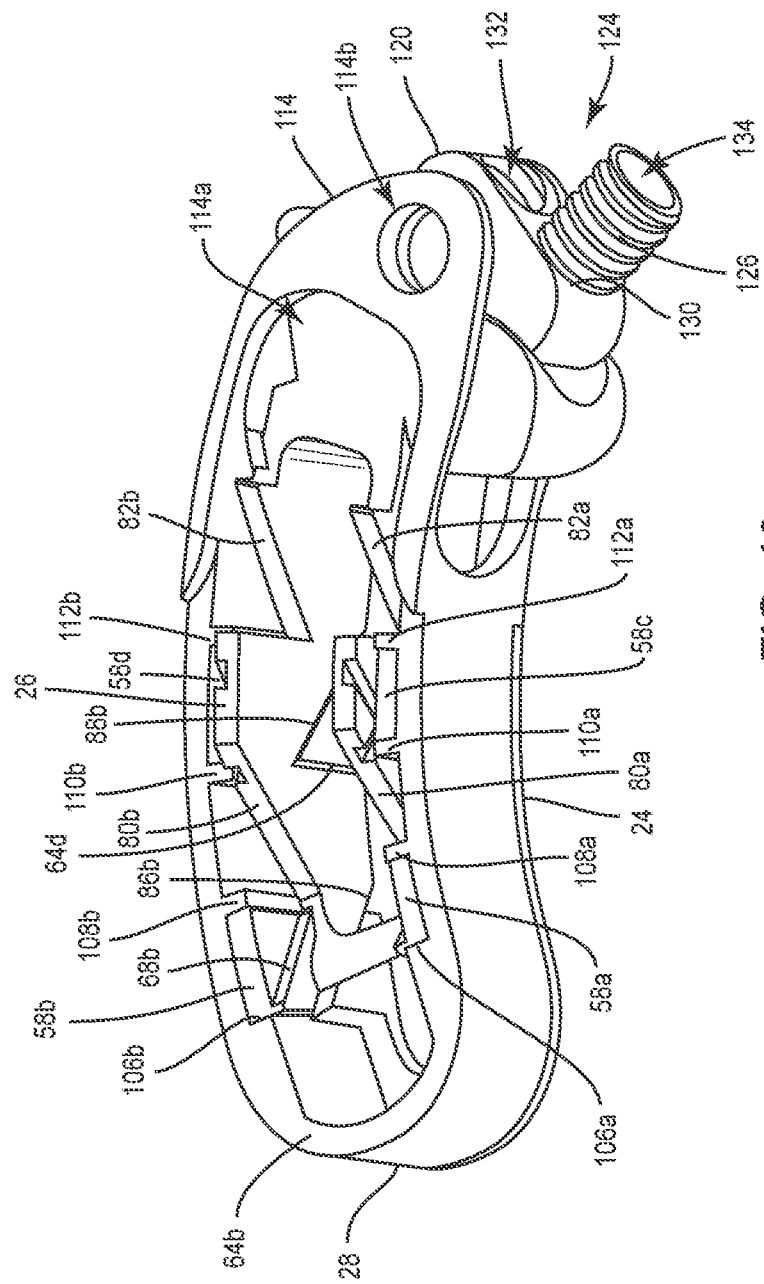
FIG. 16 is a top, perspective view of components of the implant shown in FIG. 1.

Tab 38a is positioned between rail 108a and rail 110a such that side surfaces of tab 38a engage a side surface of rail 108a and a side surface of rail 110a, as shown in FIG. 15. Tab 38b is positioned between rail 108b and rail 110b such that side surfaces of tab 38b engage a side surface of rail 108b and a side surface of rail 110b, as shown in FIG. 15. Tab 38c is positioned between rail 112a and end 102 such that a side surface of tab 38c engages a side surface of rail 112a, as shown in FIG. 15. Tab 38d is positioned between rail 112b and end 102 such that a side surface of tab 38d engages a side surface of rail 112b, as shown in FIG. 15. Tab 58a is positioned between flange 106a and rail 108a such that side surfaces of tab 58a engage flange 106a and a side surface of rail 108a, as shown in FIG. 16. Tab 58b is positioned between flange 106b and rail 108b such that side surfaces of tab 58b engage flange 106b and a side surface of rail 108a, as shown in FIG. 16. Tab 58c is positioned between rail 110a and rail 112a such that side surfaces of tab 58c engage a side surface of rail 110a and a side surface of rail 112a, as shown in FIG. 16. Tab 58d is positioned between rail 110b and rail 112b such that side surfaces of tab 58d engage a side surface of rail 110b and a side surface of rail 112b, as shown in FIG. 16.

As implant 20 moves from the undeployed or unexpanded configuration, shown in FIGS. 1 and 2, to the deployed or expanded configuration, shown in FIGS. 3 and 4, tab 38a moves in the space between rail 108a and rail 110a in the direction shown by arrow A in FIGS. 1 and 3, tab 38b moves in the space between rail 108b and rail 110b in the direction shown by arrow A, tab 38c moves in the space between rail 112a and end 102 in the direction shown by arrow A, and tab 38d moves in the space between rail 112b and end 102 in the direction shown by arrow A, as discussed herein. As implant 20 moves from the undeployed or unexpanded configuration to the deployed or expanded configuration, tab 58a moves in the space between flange 106a and rail 108a in the direction shown by arrow B in FIGS. 1 and 3, tab 58b moves in the space between flange 106b and rail 108b in the direction shown by arrow B, tab 58c moves in the space between rail 110a and rail 112a in the direction shown by arrow B, and tab 58d moves in the space between rail 110b and rail 112b in the direction shown by arrow B, as discussed herein.

As implant 20 moves from the deployed or expanded configuration, shown in FIGS. 3 and 4, to the undeployed or unexpanded configuration, shown in FIGS. 1 and 2, tab 38a moves in the space between rail 108a and rail 110a in the direction shown by arrow B in FIGS. 1 and 3, tab 38b moves in the space between rail 108b and rail 110b in the direction shown by arrow B, tab 38c moves in the space between rail 112a and end 102 in the direction shown by arrow B, and tab 38d moves in the space between rail 112b and end 102 in the direction shown by arrow B, as discussed herein. As implant 20 moves from the deployed or expanded configuration to the undeployed or unexpanded configuration, tab 58a moves in the space between flange 106a and rail 108a in the direction shown by arrow A in FIGS. 1 and 3, tab 58b moves in the space between flange 106b and rail 108b in the direction shown by arrow A, tab 58c moves in the space between rail 110a and rail 112a in the direction shown by arrow A, and tab 58d moves in the space between rail 110b and rail 112b in the direction shown by arrow A, as discussed herein.

End 102 of frame 28 comprises a wall 114, and a wall 116 that is spaced apart from wall 114 by a wall 118 of frame 28, as shown in FIG. 13. Wall 114 comprises an opening 114a and wall 116 comprises an opening 116a. Openings 114a, 116a are coaxial and are in communication with interior cavity 104. Wall 114 comprises an opening, such as, for example, a throughhole 114b and wall 116 comprises an opening, such as, for example, a throughhole 116b. Throughhole 114b is coaxial with throughhole 116b. Throughholes 114b, 116b are each configured for disposal of a portion of a pivot 120 of implant 20, as discussed herein.

Figure 17:
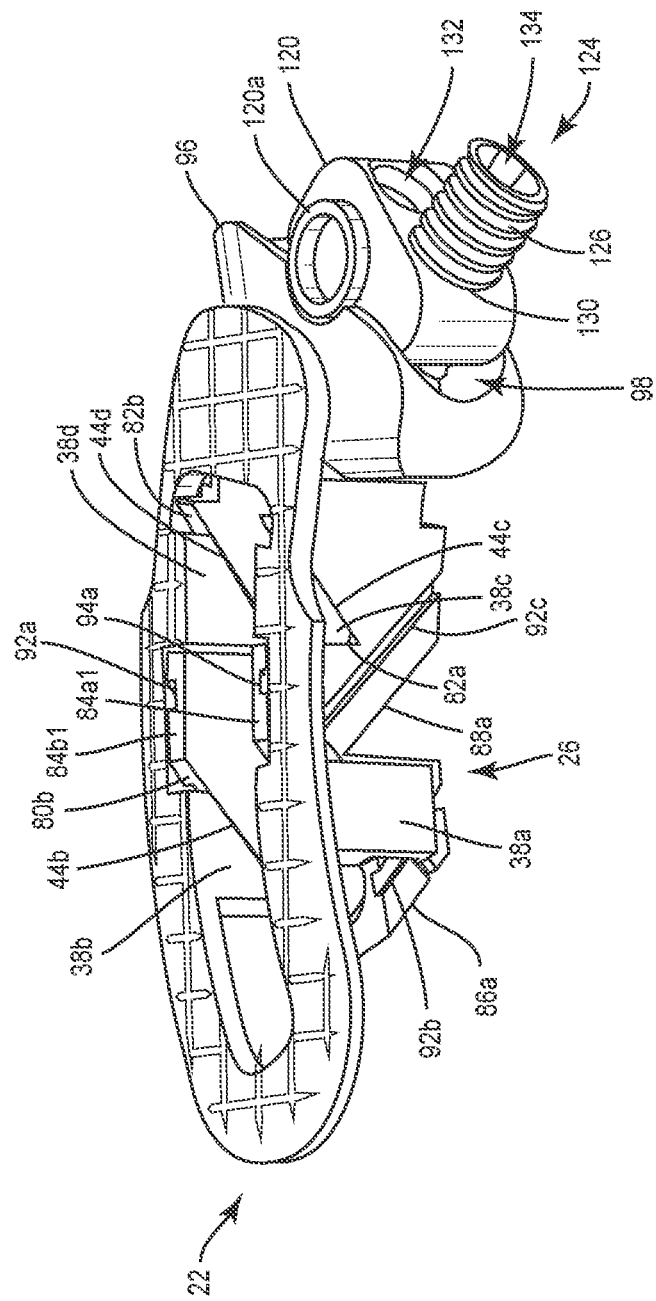
FIG. 17 is a side, perspective view of components of the implant shown in FIG. 1.
Figure 18:
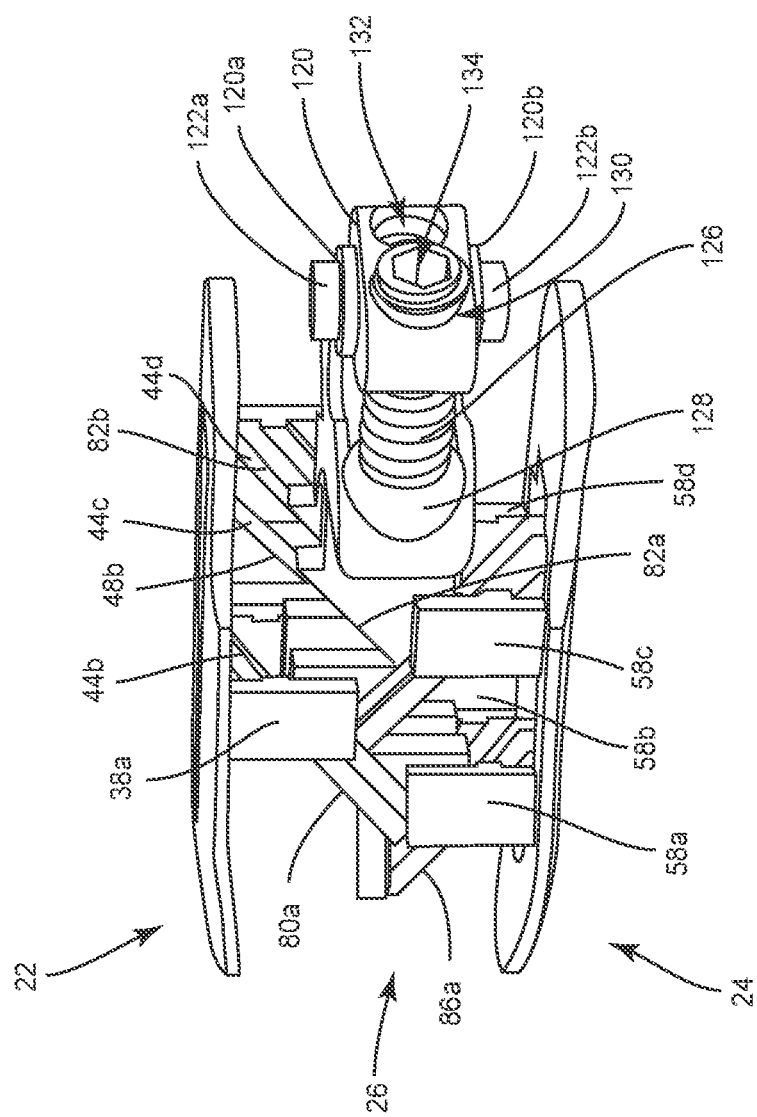
FIG. 18 is a side, perspective view of components of the implant shown in FIG. 1.

Pivot 120 is positioned within frame 28 between wall 114 and wall 116 such that a top surface of pivot 120 is spaced apart from a bottom surface of wall 114, and a bottom surface of pivot 120 is spaced apart from a top surface of wall 116. In some embodiments, end 72 of wedge 26 comprises a cutout 96a that extends through a top surface of end wall 96 of wedge 26 and a cutout 96b that extends through a bottom surface of end wall 96, as shown in FIG. 9, for example. Cutout 96a is aligned with cutout 96b. In some embodiments, cutouts 96a, 96b each have an arcuate configuration. In some embodiments, cutouts 96a, 96b each have a semi-circular configuration. Pivot 120 comprises a flange, such as, for example, a ring 120a that extends outwardly from the top surface of pivot 120 and a flange, such as, for example, a ring 120*b* that extends from the bottom surface of pivot 120, as shown in FIGS. 17 and 18. In some embodiments, ring 120*b* is similar or identical to ring 120*a*. A portion of ring 120*a* is positioned within cutout 96*a* of wedge 26 such that a top surface of ring 120*a* engages the bottom surface of wall 114. A portion of ring 120*b* is positioned within cutout 96*b* of wedge 26 such that a bottom surface of ring 120*a* engages the top surface of wall 116.

Implant 20 comprises a pivot plug 122*a* that extends through throughhole 114*b* and into ring 120*a*, and a pivot plug 122*b* that extends through throughhole 116*b* and into ring 120*b*. In some embodiments, pivot plug 122*a* is fixed relative to ring 120*a* and pivot plug 122*b* is fixed relative to ring 120*b*. In some embodiments, pivot plug 122*a* is removable from ring 120*a* and pivot plug 122*b* is removable from ring 120*b*. In some embodiments, pivot plug 122*a* and ring 120*a* are monolithic and pivot plug 122*b* and ring 120*b* are monolithic. Pivot 120 is pivotable relative to endplates 22, 24, wedge 26 and frame 28. In some embodiments, pivot 120 is configured to pivot about 85 degrees relative to endplates 22, 24, wedge 26 and frame 28 to allow an insertion instrument to articulate about 85 degrees relative to implant 20, as discussed herein. As pivot 120 pivots relative to endplates 22, 24, wedge 26 and frame 28, ring 120*a* rotates within cutout 96*a*, pivot plug 122*a* rotates within throughhole 114*b*, ring 120*b* rotates within cutout 96*b* and pivot plug 122*b* rotates within throughhole 116*b*.

Implant 20 comprises an actuator 124 that is coupled to pivot 120 and engages wedge 26. Actuator 124 is a screw, such as, for example, a ball-tipped drive screw having a threaded shank 126 and a ball tip 128 that is coupled to shank 126. Shank 126 extends through a threaded passageway 130 in pivot 120 such that tip 128 is positioned within trough 98. An end of shank 126 defines a tool socket 134 configured for disposal of a bit of a driver. In some embodiments, socket 134 may have a cruciform, Phillips, square, hexagonal, polygonal, star or hexalobe cross sectional configuration. It is envisioned that socket 134 may have any configuration that allows the tip of the driver to mate with socket 134 such that rotation of the driver rotates shank 126.

Through holes and slots may be provided in the components described to allow injection of graft material from outside the interbody device 20 into openings and cavities (39, 59 and 78) to promote fusion. The graft material may be transported from outside the incision into one or more openings or cavities, or may be loaded at an intermediary holding chamber, for example, within the inserter midway into the incision, then injected or passed into the cavity. Such transport may comprise, for example, providing a loading tube integral to the actuator driver to provide flow into a central hole in actuator 124, then into a slot within recess 98 on wedge 26, then into the common cavity of components 22, 24 and 26. It is contemplated that the graft material may flow into the common cavity, then ports provided in outer wall 118 of end 100 to allow the graft to flow into the interbody space. Anchoring features may also be included to allow flow from outside the device into the disc space directly, bypassing the device altogether.

In operation and use, the interbody implant system is employed with a surgical procedure, such as, a fusion treatment of a spine of a patient including vertebrae and body areas adjacent thereto, as discussed herein. The interbody implant system may also be employed with other surgical procedures, such as, for example, discectomy, laminotomy, laminectomy, nerve root retraction, foramenotomy, facetectomy, decompression, and spinal, nucleus or disc replacement.

For example, the interbody implant system can be employed with a surgical arthrodesis procedure, such as, for example, an interbody fusion for treatment of an applicable condition or injury of an affected section of a spinal column and adjacent areas within a body, such as, for example, an intervertebral disc space between a first vertebra and a second vertebra. It is contemplated that intervertebral implant 20 of the interbody implant system, described above, can be inserted within the intervertebral disc space to space apart articular joint surfaces, provide support and maximize stabilization of the vertebrae. It is further contemplated that intervertebral implant 20 provides height restoration between vertebral bodies, decompression, restoration of sagittal balance and/or resistance of subsidence into vertebral endplates.

In use, to treat the affected section of the vertebrae, a medical practitioner obtains access to a surgical site including the vertebrae in any appropriate manner, such as through incision and retraction of tissues. It is envisioned that the interbody implant system can be used in any existing surgical method or technique including open surgery, mini-open surgery, minimally invasive surgery and percutaneous surgical implantation, whereby the vertebrae are accessed through a mini-incision or sleeve that provides a protected passageway to the area. Once access to the surgical site is obtained, the particular surgical procedure is performed for treating the spine disorder. Intervertebral implant 20, described above, is then employed to augment the surgical treatment. Intervertebral implant 20 can be delivered or implanted as a pre-assembled device or can be assembled in situ. Intervertebral implant 20 can be completely or partially revised, removed or replaced in situ. It is contemplated that one or all of the components of the interbody implant system can be delivered to the surgical site via manual manipulation and/or a free hand technique. It is further contemplated that intervertebral implant 20 may be inserted posteriorly, and then manipulated anteriorly and/or lateral and/or medial.

An incision is made in the body of a patient and a cutting instrument creates a surgical pathway for implantation of intervertebral implant 20 within the patient body. A guide instrument (not shown) is employed to initially distract the first vertebra from the second vertebra. A sleeve or cannula is used to access the intervertebral disc space and facilitate delivery and access for components of the interbody implant system. A preparation instrument can be inserted within the sleeve or cannula and disposed within the intervertebral disc space. The preparation instrument(s) can be employed to remove some or all of the disc tissue including the disc nucleus and fluids, adjacent tissues and/or bone, corticate, scrape and/or remove tissue from the surfaces of endplates of the first and second vertebrae, as well as for aspiration and irrigation of the region according to the requirements of a particular surgical application.

Intervertebral implant 20 is inserted into the patient with implant 20 disposed in the undeployed or unexpanded configuration shown in FIGS. 1 and 2. Implant 20 is delivered along the surgical pathway using a substantially posterior approach to position implant 20 within the intervertebral disc space. In some embodiments, an end of an inserter is positioned within a threaded passageway 132 in pivot 120 to couple implant 20 with the inserter. In some embodiments, the end of the inserter includes a threaded tip that mates with threaded passageway 132 of pivot 120 to couple implant 20 with the inserter. Passageway 130 is spaced apart from passageway 132 by an inner wall of pivot 120. The inserter is then manipulated to deliver implant 20 into the prepared intervertebral disc space, between the first vertebra and the second vertebra, according to the requirements of a particular surgical application. In some embodiments, portions 84*a*1, 84*b*1 of wedge 26 are flush with engagement surface 34 of endplate 22 when implant 20 is in the undeployed or unexpanded configuration, as shown in FIG. 17, for example. In some embodiments, portions 90*a*1, 90*b*1 of wedge 26 are flush with engagement surface 54 of endplate 24 when implant 20 is in the undeployed or unexpanded configuration Once implant 20 is positioned within the intervertebral disc space, implant 20 may be moved within the intervertebral disc space such that implant 20 is positioned within the intervertebral disc space at a selected angle by moving pivot 120 such that pivot 120 rotates relative to endplates 22, 24, wedge 26 and frame 28. That is, implant 20 may be rotated within the intervertebral disc space by articulating pivot 120 to rotate pivot 120 relative to endplates 22, 24, wedge 26 and frame 28. In some embodiments, pivot 120 is rotated relative to endplates 22, 24, wedge 26 and frame 28 by manipulating the inserter. Pivot 120 may be articulated between about 15 degrees and about 85 degrees relative to endplates 22, 24, wedge 26 and frame 28. In some embodiments, pivot 120 is articulated relative to endplates 22, 24, wedge 26 and frame 28 such that implant 120 is disposed at a selected angle relative to the inserter before positioning implant 20 within the intervertebral disc space. Implant 20 is then inserted into the intervertebral disc space with implant 20 at the selected angle relative to the inserter to position implant 20 at a selected angle within the intervertebral disc space. Once implant 20 is positioned within the intervertebral disc space with implant 20 at the selected angle, the inserter can be uncoupled from implant 20 by rotating the inserter relative to pivot 120 such that the threaded tip of the inserter backs out of passageway 132 of pivot 120.

Upon desired positioning of intervertebral implant 20 within the intervertebral disc space, the tip of the driver is inserted into socket 134 to mate features of the tip of the driver with features of socket 134 such that rotation of the driver rotates actuator 124 relative to pivot 120. Implant 20 is then deployed within the intervertebral disc space to move implant 20 from the undeployed or unexpanded configuration, shown in FIGS. 1 and 2, to the deployed or expanded configuration, shown in FIGS. 3 and 4. The driver is rotated in a first rotational direction, such as, for example, clockwise or counterclockwise such that actuator 124 moves relative to pivot 120 in the direction shown by arrow C in FIGS. 1 and 3. As actuator 124 moves in the direction shown by arrow C, tip 128 of actuator 124 pushes against the inner surface of end wall 96 that defines trough 98 such that wedge 26 moves relative to endplates 22, 24 and frame 28 in the direction shown by arrow C. As wedge 26 moves relative to endplates 22, 24 and frame 28 in the direction shown by arrow C, ramp 44*a* engages and translates along ramp 80*a*, ramp 44*b* engages and translates along ramp 80*b*, ramp 44*c* engages and translates along ramp 82*a* and ramp 44*d* engages and translates along ramp 82*b* to move endplate 22 relative to wedge 26 and frame 28 in the direction shown by arrow A in FIGS. 1 and 3. As wedge 26 moves relative to endplates 22, 24 and frame 28 in the direction shown by arrow C, ramp 64*a* engages and translates along ramp 86*a*, ramp 64*b* engages and translates along ramp 86*b*, ramp 64*c* engages and translates along ramp 88*a* and ramp 64*d* engages and translates along ramp 88*b* to move endplate 24 relative to wedge 26 and frame 28 in the direction shown by arrow B in FIGS. 1 and 3.

Engagement surface 34 of endplate 22 is spaced apart a first distance from engagement surface 54 of endplate 24 when implant 20 is the undeployed or unexpanded configuration. Engagement surface 34 is spaced apart an increased second distance from engagement surface 54 when implant 20 is the deployed or expanded configuration, shown in FIGS. 3 and 4. In some embodiments, the first distance is about 7 mm and the second distance is at least about 14 mm. In some embodiments, the first distance is about 8 mm and the second distance is at least about 16 mm. In some embodiments, the first distance is about 9 mm and the second distance is at least about 18 mm.

As implant 20 moves from the undeployed or unexpanded configuration to the deployed or expanded configuration, endplate 22 moves away from endplate 24 such that engagement surface 34 of endplate 22 engages the first vertebra and engagement surface 54 of endplate 24 engages the second vertebra. Endplates 22, 24 push against the vertebrae to move the first vertebra away from the second vertebra and increase the size of the intervertebral disc space. It is contemplated that in the deployed or expanded configuration, intervertebral implant 20 provides height restoration between the first vertebra and the second vertebra, decompression, restoration of sagittal balance and resistance of subsidence into the endplates of the vertebrae. Implant 20 may be kept in the deployed or expanded configuration to maintain the increased size of the intervertebral disc space In some embodiments, a material, such as, for example, bone graft is positioned within cavity 78 of wedge 26 to promote bone growth to fuse the first vertebra with the second vertebra. In some embodiments, engagement surface 34 extends parallel to engagement surface 54 when implant 20 is in the deployed or expanded configuration. In some embodiments, engagement surface 34 extends transverse to engagement surface 54 when implant 20 is in the deployed or expanded configuration. It is envisioned that the ramps of endplates 22, 24 and wedge 26 can be configured such that engagement surface 34 extends at any angle between about 0 degrees and about 90 degrees relative to engagement surface 54 when implant 20 is in the deployed or expanded configuration.

In one embodiment, the bone graft can be a particulate material, which may include an osteoconductive material such as HA and/or an osteoinductive agent such as a bone morphogenic protein (BMP) to enhance bony fixation of intervertebral implant 20 with the adjacent vertebrae. It is contemplated that the bone graft may include therapeutic polynucleotides or polypeptides. It is further contemplated that the agent and/or bone graft may include biocompatible materials, such as, for example, biocompatible metals and/or rigid polymers, such as, titanium elements, metal powders of titanium or titanium compositions, sterile bone materials, such as allograft or xenograft materials, synthetic bone materials such as coral and calcium compositions, such as HA, calcium phosphate and calcium sulfite, biologically active agents, for example, gradual release compositions such as by blending in a bioresorbable polymer that releases the biologically active agent or agents in an appropriate time dependent fashion as the polymer degrades within the patient. Suitable biologically active agents include, for example, BMP, Growth and Differentiation Factors proteins (GDF) and cytokines. Implant 20 can be made of radiolucent materials such as polymers. Radiomarkers may be included for identification under x-ray, fluoroscopy, CT or other imaging techniques. It is envisioned that the bone graft may include one or a plurality of therapeutic agents and/or pharmacological agents for release, including sustained release, to treat, for example, pain, inflammation and degeneration.

It is envisioned that the components of the interbody implant system, which may include one or a plurality of intervertebral implants 20, can be delivered to the surgical site via alternate approaches. In one embodiment, intervertebral implant 20 is delivered through the surgical pathway along a transforaminal lumbar interbody fusion approach into the intervertebral disc space and disposed in the deployed or expanded configuration. In one embodiment, a plurality of intervertebral implants 20 are delivered through the surgical pathway along a posterior lumbar interbody fusion approach into the intervertebral disc space and disposed in the deployed or expanded configuration in a side by side orientation.

In one embodiment, intervertebral implant 20 can be collapsed from the deployed or expanded configuration to an alternate configuration between the deployed or expanded configuration and the undeployed or unexpanded configuration, to collapse intervertebral implant 20 as may be desired to reposition with or remove intervertebral implant 20 from the intervertebral disc space. In one embodiment, the interbody implant system includes a plurality of intervertebral implants 20, which can be variously sized and configured, and/or oriented in a side by side engagement, spaced apart and/or staggered.

Implant 20 may be moved from the deployed or expanded configuration to the undeployed or unexpanded configuration by rotating the driver in a second rotational direction, such as, for example, clockwise or counterclockwise such that actuator 124 moves relative to pivot 120 in the direction shown by arrow D in FIGS. 1 and 3. As actuator 124 moves in the direction shown by arrow D, tip 128 of actuator 124 pulls end wall 96 of wedge 26 in the direction shown by arrow D such that wedge 26 moves relative to endplates 22, 24 and frame 28 in the direction shown by arrow D. As wedge 26 moves relative to endplates 22, 24 and frame 28 in the direction shown by arrow D, ramp 44a engages and translates along ramp 80a, ramp 44b engages and translates along ramp 80b, ramp 44c engages and translates along ramp 82a and ramp 44d engages and translates along ramp 82b to move endplate 22 relative to wedge 26 and frame 28 in the direction shown by arrow B in FIGS. 1 and 3. As wedge 26 moves relative to endplates 22, 24 and frame 28 in the direction shown by arrow D, ramp 64a engages and translates along ramp 86a, ramp 64b engages and translates along ramp 86b, ramp 64c engages and translates along ramp 88a and ramp 64d engages and translates along ramp 88b to move endplate 24 relative to wedge 26 and frame 28 in the direction shown by arrow A in FIGS. 1 and 3. Once implant 20 is in the undeployed or unexpanded configuration implant 20 can be moved within the intervertebral disc space and/or removed from the intervertebral disc space, as desired.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A device to space apart vertebral members comprising:
an upper endplate comprising a first engagement surface configured to engage a first vertebra and an opposite inner surface, the upper endplate comprising first projections extending from the inner surface, the first projections each comprising a first inclined surface;
a lower endplate comprising a second engagement surface configured to engage a second vertebra that is adjacent to the first vertebra and an opposite inner surface, the lower endplate comprising second projections extending from the inner surface of the lower endplate, the second projections each comprising a second inclined surface;
a wedge positioned between the endplates, the wedge comprising first mating parts that engage the first inclined surfaces and second mating parts that engage the second inclined surfaces,
wherein the wedge is movable relative to the endplates to move the device between a first configuration having a first height between the engagement surfaces and a second configuration having an increased second height between the engagement surfaces,
the device comprising a frame having an interior cavity, at least a portion of the endplates and the wedge being positioned within the interior cavity as the device moves between the first and second configurations, the frame comprising a plurality of rails that define recesses therebetween, the projections each being disposed in one of the recesses such that side surfaces of the projections engage two of the rails and the projections translate within the recesses as the device moves between the first and second configurations,
the device comprising a pivot coupled to the frame and an actuator that extends through the pivot, wherein rotation of the actuator relative to the pivot translates the actuator to move the wedge to move the device between the first and second configurations.

2. A device as recited in claim 1, wherein the first mating parts are first ramps defined by an upper surface of the wedge and the second mating parts are second ramps defined by a lower surface of the wedge.

3. A device as recited in claim 2, wherein a portion of the upper surface is flush with the first engagement surface when the device is in the first configuration.

4. A device as recited in claim 2, wherein:
the wedge includes a centerline positioned equidistant from the upper and lower surfaces; and
the first mating parts are ramps that each extend from the upper surface to a portion of the wedge below the centerline.

5. A device as recited in claim 2, wherein:
the wedge includes a centerline positioned equidistant from the upper and lower surfaces; and
the second mating parts are ramps that each extend from the lower surface to a portion of the wedge above the centerline.

6. A device as recited in claim 1, wherein the first inclined surfaces each extend transverse to a longitudinal axis defined by the first engagement surface and the second inclined portions each extend transverse to a longitudinal axis defined by the second engagement surface.

7. A device as recited in claim 1, wherein the first projections are spaced apart from one another by an opening that extends through the first engagement surface and the inner surface of the upper endplate and the second projections are spaced apart from one another by an opening that extends through the second engagement surface and the inner surface of the lower endplate.

8. A device as recited in claim 1, wherein the first projections comprise a first pair of first projections and a second pair of first projections that are spaced apart from the first pair of first projections, and the second projections comprise a first pair of second projections and a second pair of second projections that are spaced apart from the first pair of second projections.

9. A device as recited in claim 1, wherein the second height is at least two times greater than the first height.

10. A device as recited in claim 1, wherein the wedge comprises a sidewall including grooves, at least one of the first projections and at least one of the second projections including an outrigger that is positioned within one of the grooves.

11. A device as recited in claim 10, wherein one of the grooves intersects another one of the grooves.

12. A device as recited in claim 1, wherein the first engagement surface extends parallel to the second engagement surface when the device is in the first and second configurations.

13. A device as recited in claim 1, wherein the pivot is configured to rotate between 15 degrees and 85 degrees relative to the frame.

14. A device as recited in claim 1, wherein the pivot includes a first flange positioned in an opening in an upper surface of the wedge and a second flange that is positioned in an opening in a lower surface of the wedge.

15. A device as recited in claim 1, wherein the actuator is a screw having a ball tip, the ball tip being positioned within an arcuate track in the wedge.

16. A device to space apart vertebral members comprising:
- an upper endplate comprising a first engagement surface and an opposite inner surface, the upper endplate comprising first and second pairs of first projections extending from the inner surface, the first projections each comprising a first inclined surface;
- a lower endplate comprising a second engagement surface and an opposite inner surface, the lower endplate comprising first and second pairs of second projections extending from the inner surface of the lower endplate, the second projections each comprising a second inclined surface;
- a wedge positioned between the endplates, the wedge comprising an upper surface having first ramps that engage the first inclined surfaces and a lower surface having second ramps that engage the second inclined surfaces,
- wherein the wedge is movable relative to the endplates such that the inclined surfaces translate along the ramps to move the device between a first configuration having a first height between the engagement surfaces and a second configuration having an increased second height between the engagement surfaces,
- the device comprising a frame having an interior cavity, at least a portion of the endplates and the wedge being positioned within the interior cavity as the device moves between the first and second configurations, the frame comprising a plurality of rails that define recesses therebetween, the projections each being disposed in one of the recesses such that side surfaces of the projections engage two of the rails and the projections translate within the recesses as the device moves between the first and second configurations,
- the device comprising a pivot coupled to the frame and an actuator that extends through the pivot, wherein rotation of the actuator relative to the pivot translates the actuator to move the wedge to move the device between the first and second configurations.

17. A device to space apart vertebral members comprising:
- an upper endplate comprising a first engagement surface and an opposite inner surface, the upper endplate comprising first and second pairs of first projections extending from the inner surface, the first projections each comprising a first inclined surface;
- a lower endplate comprising a second engagement surface and an opposite inner surface, the lower endplate comprising first and second pairs of second projections extending from the inner surface of the lower endplate, the second projections each comprising a second inclined surface;
- a wedge positioned between the endplates, the wedge comprising an upper surface having first ramps that engage the first inclined surfaces and a lower surface having second ramps that engage the second inclined surfaces,
- wherein the wedge is movable relative to the endplates such that the inclined surfaces translate along the ramps to move the device between a first configuration having a first height between the engagement surfaces and a second configuration having an increased second height between the engagement surfaces,
- wherein a portion of the upper surface is flush with the first engagement surface when the device is in the second configuration,
- the device comprising a frame having an interior cavity, at least a portion of the endplates and the wedge being positioned within the interior cavity as the device moves between the first and second configurations, the frame comprising a plurality of rails that define recesses therebetween, the projections each being disposed in one of the recesses such that side surfaces of the projections engage two of the rails and the projections translate within the recesses as the device moves between the first and second configurations,
- the device comprising a pivot coupled to the frame and an actuator that extends through the pivot, wherein rotation of the actuator relative to the pivot translates the actuator to move the wedge to move the device between the first and second configurations.

* * * * *

UNITED STATES PATENT AND TRADEMARK OFFICE
CERTIFICATE OF CORRECTION

PATENT NO. : 10,111,755 B2
APPLICATION NO. : 15/442101
DATED : October 30, 2018
INVENTOR(S) : Foley et al.

Page 1 of 1

It is certified that error appears in the above-identified patent and that said Letters Patent is hereby corrected as shown below:

In the Specification

In Column 2, Line 14, delete "he" and insert -- the --, therefor.

In Column 5, Lines 54-67, delete "In addition, treating or treatment does not require complete alleviation of signs or symptoms, does not require a cure, and specifically includes procedures that have only a marginal effect on the patient. Treatment can include inhibiting the disease, for example, arresting its development, or relieving the disease, for example, causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise." and insert the same at Line 53 after "having it)." as a continuation paragraph.

In Column 6, Lines 35-36, delete "polyimide, polyimide," and insert -- polyamide, polyimide, --, therefor.

In Column 7, Line 65, delete "ramps," and insert -- ramps. --, therefor.

In Column 8, Lines 18-19, delete "di almost" and insert -- distalmost --, therefor.

In Column 14, Line 3, delete "86band" and insert -- 86b and --, therefor.

In Column 19, Line 28, delete "implant 120" and insert -- implant 20 --, therefor.

Signed and Sealed this
Seventeenth Day of March, 2020

Andrei Iancu
*Director of the United States Patent and Trademark Office*